(12) United States Patent
Yang et al.

(10) Patent No.: US 12,741,879 B2
(45) Date of Patent: Sep. 22, 2026

(54) SILICON-ALUMINUM ZEOLITE SCM-36, MANUFACTURING METHOD THEREFOR AND APPLICATION THEREOF

(71) Applicants: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

(72) Inventors: Weimin Yang, Shanghai (CN); Zhendong Wang, Shanghai (CN); Duozheng Ma, Shanghai (CN); Songlin Liu, Shanghai (CN); Chuang Liu, Shanghai (CN); Xiangcheng Li, Shanghai (CN); Zhiqing Yuan, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

( * ) Notice: Subject to any disclaimer, the term of this patent is extended or adjusted under 35 U.S.C. 154(b) by 274 days.

(21) Appl. No.: 18/696,685

(22) PCT Filed: Oct. 8, 2022

(86) PCT No.: PCT/CN2022/123784

§ 371 (c)(1),
(2) Date: Mar. 28, 2024

(87) PCT Pub. No.: WO2023/061256

PCT Pub. Date: Apr. 20, 2023

(65) Prior Publication Data

US 2024/0409421 A1 Dec. 12, 2024

(30) Foreign Application Priority Data

Oct. 11, 2021 (CN) .......................... 202111184012.0
Oct. 22, 2021 (CN) .......................... 202111233138.2

(51) Int. Cl.
*C01B 39/48* (2006.01)
*B01J 29/70* (2006.01)
(Continued)

(52) U.S. Cl.
CPC ............... *C01B 39/48* (2013.01); *B01J 29/70* (2013.01); *B01J 35/615* (2024.01); *B01J 35/635* (2024.01);
(Continued)

(58) Field of Classification Search
CPC .......... C01B 39/48; C07C 2/865; C07C 2/867
See application file for complete search history.

(56) References Cited

U.S. PATENT DOCUMENTS 2,882,244 A 4/1959 Milton
3,130,007 A 4/1964 Breck
(Continued)

FOREIGN PATENT DOCUMENTS

CN 103435062 A 12/2013
CN 112239215 A 1/2021
(Continued)

*Primary Examiner* — James C Goloboy
(74) *Attorney, Agent, or Firm* — NKL Law; Allen Xue

(57) ABSTRACT

A silicon-aluminum zeolite SCM-36, a manufacturing method therefor and an application thereof are provided. The zeolite has a silicon/aluminum ratio n≥5, and has a distinctive XRD diffraction spectrum. The SCM-36 zeolite can be used as an adsorbent, a catalyst, or a catalyst carrier.

20 Claims, 10 Drawing Sheets

(51) Int. Cl.
*B01J 35/61* (2024.01)
*B01J 35/63* (2024.01)
*B01J 37/08* (2006.01)
*C07C 2/86* (2006.01)

(52) U.S. Cl.
CPC ............... *B01J 37/08* (2013.01); *C07C 2/865* (2013.01); *C07C 2/867* (2013.01); *B01J 2235/15* (2024.01); *C01P 2002/74* (2013.01); *C01P 2006/12* (2013.01); *C01P 2006/14* (2013.01)

(56) References Cited

U.S. PATENT DOCUMENTS

| | | | | |
|---|---|---|---|---|
| 3,702,886 | A | 11/1972 | Argauer et al. | |
| 4,410,501 | A | 10/1983 | Taramasso et al. | |
| 4,439,409 | A | 3/1984 | Puppe et al. | |
| 4,954,325 | A | 9/1990 | Rubin et al. | |
| 5,362,697 | A | 11/1994 | Fung et al. | |
| 6,162,416 | A | 12/2000 | Gajda et al. | |
| 9,504,995 | B2 * | 11/2016 | Burton | B01J 29/70 |

FOREIGN PATENT DOCUMENTS

| | | | |
|---|---|---|---|
| CN | 112624149 | A | 4/2021 |
| CN | 112645351 | A | 4/2021 |
| JP | 2012031009 | A | 2/2012 |
| JP | 2016536240 | A | 11/2016 |
| JP | 2017210399 | A | 11/2017 |
| JP | 2021523082 | A | 9/2021 |
| WO | 2016145618 | A1 | 9/2016 |
| WO | 2018199714 | A1 | 11/2018 |
| WO | 2020250985 | A1 | 12/2020 |

* cited by examiner

SILICON-ALUMINUM ZEOLITE SCM-36, MANUFACTURING METHOD THEREFOR AND APPLICATION THEREOF

TECHNICAL FIELD

The present application relates to the technical field of zeolites, particularly to a silicon-aluminum zeolite, a manufacturing method therefor and an application thereof.

BACKGROUND ART

In industry, zeolite materials are widely used in fields such as catalysis, ion exchange, adsorption and separation due to their hollow structure and large surface area. Subtle differences in the structures of these materials indicate differences in various observable properties used to characterize these materials, such as their morphology, specific surface area, pore size and variability of these sizes. In the meanwhile, the differences also imply significant differences in the catalytic and adsorption properties of the materials themselves.

The basic framework structure of a crystalline microporous zeolite is based on a rigid three-dimensional $TO_4$ ($SiO_4$, $AlO_4$ etc.) unit structure; in this structure, $TO_4$ shares oxygen atoms in a tetrahedral manner, and the charge balance of the framework tetrahedron such as $AlO_4$ is maintained through the presence of surface cations such as $Na^+$ and $H^+$. It is thus clear that the framework properties of zeolite can be changed through cation exchange. At the same time, there are abundant pore channel systems with a certain pore size in the zeolite structure. These pore channels are interwoven to form a three-dimensional network structure, and the framework can still exist stably after the removal of water or organic matters in the pores (U.S. Pat. No. 4,439,409). Based on the above structure, zeolite not only exhibits excellent catalytic activity and shape selectivity for various organic reactions, but also achieves a good selectivity through modification (U.S. Pat. Nos. 6,162,416, 4,954,325, 5,362,697).

The specific structure of a zeolite is determined by X-ray diffraction spectrum (XRD) which is determined with an X-ray powder diffractometer using a Cu-K $\alpha$ x-ray source and a nickel filter. Different zeolites differ in XRD spectrum characteristics. Known zeolites, such as A-type zeolite, Y-type zeolite, MCM-22 zeolite and the like all have a XRD spectrum with their own characteristics.

Meanwhile, zeolites with the same XRD spectrum characteristics but different types of framework elements are also different zeolites. For example, TS-1 zeolite (U.S. Pat. No. 4,410,501) and ZSM-5 zeolite (U.S. Pat. No. 3,702,886) have the same XRD spectrum characteristics, but different framework elements. Specifically, the framework elements of TS-1 zeolite are Si and Ti which have a catalytic oxidation function, while the framework elements of ZSM-5 zeolite are Si and Al, which have acid catalytic function.

In addition, zeolites having the same XRD spectrum characteristics and the same types of framework elements but different relative contents of framework elements are different zeolites. For example, X zeolite (U.S. Pat. No. 2,882,244) and Y zeolite (U.S. Pat. No. 3,130,007) have the same XRD spectrum characteristics and the same framework elements of Si and Al, but different Si/Al relative contents. Specifically, the Si/Al molar ratio of X zeolite is lower than 1.5, while the Si/Al molar ratio of Y zeolite is higher than 1.5.

CONTENTS OF INVENTION

The objective of the present application is to provide a novel silicon-aluminum zeolite (referred to as SCM-36 zeolite in the present application), a manufacturing method therefor and an application thereof. Said zeolite has specific XRD spectrum characteristics and can be used as an adsorbent, a catalyst carrier and a catalyst. It has a high selectivity to p-xylene and a cyclic stability when used as a catalyst in a reaction of 2,5-dimethylfuran and/or 2,5-hexanedione for the preparation of p-xylene.

To achieve the above objective, in one aspect, the present application provides a silicon-aluminum zeolite which has a silicon/aluminum ratio n≥5, and the X-ray diffraction spectrum of the zeolite exhibits the relative intensity characteristics of diffraction peaks as shown in a following table:

| 2θ(°) | relative intensity ($I/I_0 \times 100$) |
|---|---|
| 8.99-9.59 | s |
| 12.48-13.08 | s-vs |
| 18.91-19.51 | s-vs |
| 23.39-23.99 | m |
| 24.00-24.41 | m |
| 25.65-26.25 | vs |

In another aspect, the present application provides a method for manufacturing a silicon-aluminum zeolite, comprising the following steps:

1) crystallizing a mixture containing a silicon source, an aluminum source, an organic structure directing agent (A), an organic structure directing agent (B), an alkali source and water to obtain a zeolite; and
2) optionally, calcining the zeolite obtained in step 1);

wherein, the organic structure directing agent (A) is selected from tetramethylammonium compounds, and the organic structure directing agent (B) is selected from C6-16 alkylpyridinium compounds, n-octyltrimethylammonium compounds, or a combination thereof.

In another aspect, provided is a zeolite composition comprising the silicon-aluminum zeolite according to the present application and a binder.

In another aspect, provided is an application of the silicon-aluminum zeolite or the zeolite composition according to the present application as an adsorbent, a catalyst or a catalyst carrier.

In a further aspect, the present application provides a method for preparing p-xylene, comprising a step of reacting a raw material comprising 2,5-dimethylfuran, 2,5-hexanedione, or a combination thereof in contact with ethylene in the presence of a catalyst comprising or consisting of the silicon-aluminum zeolite of the present application.

The zeolite of the present application which has a novel structure that has not been reported in prior art can be used as an adsorbent, a catalyst carrier or a catalyst. In particular, the zeolite of the present application has a high selectivity to p-xylene and a cyclic stability when used as a catalyst in a reaction of 2,5-dimethylfuran and/or 2,5-hexanedione for the preparation of p-xylene.

MODE OF CARRYING OUT THE PRESENT INVENTION

Figure 1:
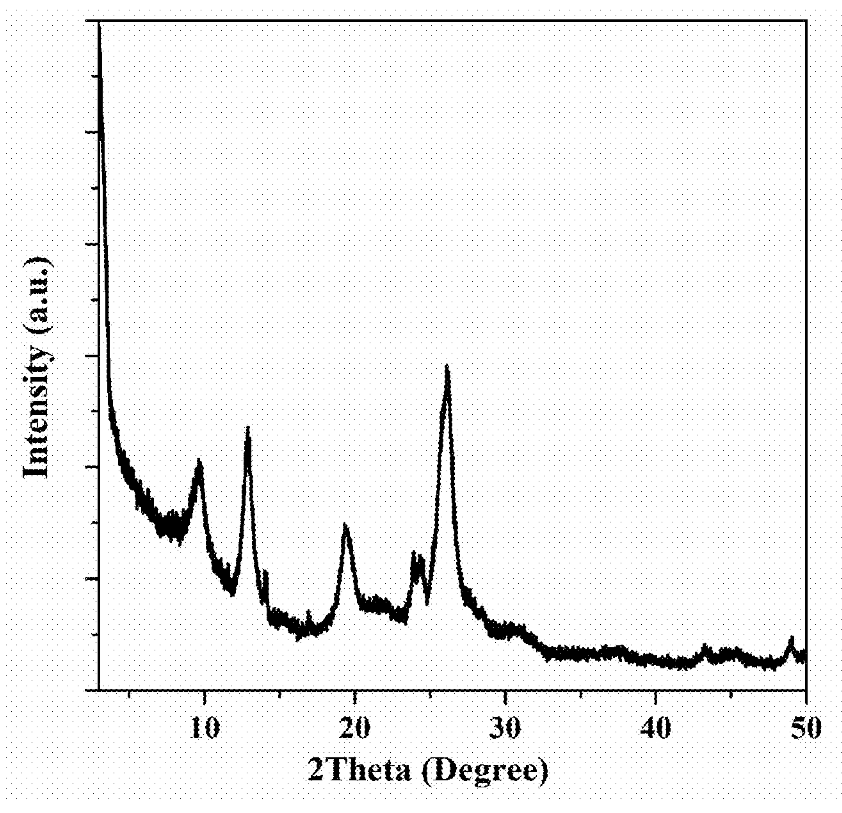
FIG. 1 illustrates the X-ray diffraction (XRD) spectrum of the zeolite obtained in Example I-1.

The specific embodiments of the present application will be explained in detail as follows. However, it should be pointed out that the scope of protection of the present application is not limited by these specific embodiments, but is determined by the claims in the annex.

All publications, patent applications, patents and other reference literatures mentioned in the present description are cited herein for reference. Unless otherwise defined, all the technical and scientific terms used in the present description have the meanings commonly understood by those skilled in the art. In case of conflicts, the definitions in the present description shall prevail.

When materials, substances, methods, steps, devices or components are introduced with a modifier of "known to those skilled in the art", "prior art" or a similar term, the objects described by the modifier include those commonly used in the art at the time of filing of the present application as well as those which are not commonly used at present but will become suitable for similar purposes as recognized in the art.

In the context of the present description, unless explicitly indicated, any matters not mentioned are all directly applicable to those known in the art without need for any changes. Moreover, any embodiments described in this present application shall all be freely combined with one or more other embodiments described herein, and the resulting technical solutions or ideas are considered as a part of the original disclosure or original recitation of the present application, but should not be considered as new contents that have not been disclosed or predicted in this present application, unless those skilled in the art believe that such combination is clearly unreasonable.

In the context of the present description, the so-called "silicon/aluminum ratio (or Si/Al ratio)" or "silicon/aluminum molar ratio (or Si/Al molar ratio)" refers to the molar ratio of silicon calculated based on $SiO_2$ and aluminum calculated based on $Al_2O_3$ in a zeolite.

In the context of the present description, the so-called "calculated based on the oxide" refers to the calculation based on a stable oxide present in the highest valence state of the corresponding element. For example, for the expression of "calculated based on the oxide", silicon refers to the calculation based on $SiO_2$, aluminum refers to the calculation based on $Al_2O_3$, titanium refers to the calculation based on $TiO_2$, boron refers to the calculation based on $B_2O_3$, zirconium refers to the calculation based on $ZrO_2$, tin refers to the calculation based on $SnO_2$, iron refers to the calculation based on $Fe_2O_3$.

In the context of the present description, with respect to a zeolite, other materials filled in the pore channel during the synthesis of the zeolite except for water and metal ions (such as organic structure directing agent molecules and the like) are referred to as "precursor" before they are removed.

In the context of the present description, the terms "synthetic state" "synthetic state form," or "zeolite in a synthetic state" refer to the state of the zeolite after the completion of the synthesis step and before the start of the post-treating step (for example a calcination step). A specific example of the synthetic state may be a state directly presented upon completion of the synthesis step, which is generally referred to as the precursor of zeolite. In view of this, the zeolite in the synthetic state may contain water and/or organic matters (particularly an organic structure directing agent).

In the context of the present description, the so-called "calcinated", "calcinated form" or "calcinated zeolite" refers to the state of the zeolite after calcination. A specific example of the state after calcination may be the state presented by further removing possible organic matters (particularly an organic structure directing agent) and water in the pore channels through calcination of the zeolite in a synthetic state.

In the context of the present description, in the XRD data of a zeolite, w, m, s, vs, w-m, m-s and s-vs etc. represent the relative intensity $I/I_0$ of the corresponding diffraction peak at angle 2θ calculated based on the diffraction peak intensity (measured in peak height) relative to the strongest diffraction peak (i.e. the diffraction peak in the highest intensity), wherein I means the peak intensity of the corresponding diffraction peak and $I_0$ means the peak intensity of the strongest diffraction peak, w represents weak, m represents moderate, s represents strong, vs represents very strong, w-m represents weak to moderate, m-s represents moderate to strong, and s-vs represents strong to very strong. Such a representation method is familiar to those skilled in the art. Generally speaking, w represents less than 20; m represents 20-40; s represents 40-70; vs represents greater than 70; w-m represents less than 40; m-s represents 20-70, and s-vs represents greater than 40.

In the context of the present description, the structure of the zeolite is determined with the X-ray diffraction spectrum after calcination at 550° C. for 5 hours. The X-ray diffraction spectrum is determined with an X-ray powder diffractometer using a Cu-K α ray source and a nickel filter. Before testing the sample, a scanning electron microscope is used to observe the crystallization of the zeolite sample to confirm that the sample only contains one type of crystal, i.e., the zeolite sample is a pure phase. Based on this, XRD test is carried out to ensure that there are no interference peaks from other crystals in the diffraction peaks of the XRD spectrum.

According to the present application, the interplanar spacing of various diffraction peaks in the XRD diffraction spectrum of the zeolite can be obtained by calculation based on the 2θ values of the diffraction peaks via Bragg Formulation: X=2d sin θ (where λ is the wavelength of the incident wave, λ=1.54 Å, d is the interplanar spacing, θ is the angle between the incident ray and the scattering plane.

In the context of the present description, the so-called "specific surface area" refers to the total surface area of a sample per unit of mass, including an internal surface area and an external surface area. A non-porous sample only has an external surface area, such as Portland cement, some clay mineral powder particles, etc. A porous sample has both an external surface area and an internal surface area, such as asbestos fibers, diatomite and zeolites. The surface area of the pores having a pore size less than 2 nanometers in the porous sample is the internal surface area, and the surface area after deducting the internal surface area is the external surface area. The external surface area of a sample per unit of mass is the external specific surface area.

In the context of the present description, the so-called "pore volume" refers to the volume of the pores of a zeolite per unit of mass. The so-called "total pore volume" refers to the volume of all the pores of a zeolite per unit of mass. The so-called "microporous volume" refers to the volume of all the micropores (generally referring to the pores having a pore channel diameter less than 2 nanometers) of a zeolite per unit of mass.

In the present application, the pore structure parameters of the zeolite material, such as the total pore volume, the micropore volume, the total specific surface area and the external specific surface area, are obtained by measuring and obtaining the nitrogen physical adsorption and desorption isotherm of the zeolite with a physical adsorption instrument (such as the TriStar 3000 physical adsorption instrument from Micromeritics in the United States), and calculating by a BET method and a t-plot method, wherein the total pore volume is the pore volume corresponding to a relative pressure $P/P_0=0.99$. The experimental conditions for the nitrogen physical adsorption and desorption are: measurement temperature −196° C., vacuum pretreatment of the zeolite at 300° C. for 10 hours before measurement, and nitrogen serving as the adsorbate.

In the context of the present description, the so-called crystal thickness refers to the average value of the thicknesses of all the plate crystals in a randomly selected observation field in the observation of a zeolite at a magnification of 100,000 times with a transmission electron microscope. The operation is repeated for a total of 10 times, and the average value of said 10 average values is taken as the crystal thickness.

As aforementioned, in the first aspect, the present application provides a silicon-aluminum zeolite, the zeolite having a silicon/aluminum ratio n≥5, wherein n is preferably in the range of 5-80, further preferably in the range of 10-65, and the X-ray diffraction spectrum of the zeolite exhibits relative intensity characteristics of diffraction peaks as shown in the table below:

| 2θ(°) | relative intensity ($I/I_0 \times 100$) |
|---|---|
| 8.99-9.59 | s |
| 12.48-13.08 | s-vs |
| 18.91-19.51 | s-vs |
| 23.39-23.99 | m |
| 24.00-24.41 | m |
| 25.65-26.25 | vs. |

In a preferred embodiment, the X-ray diffraction spectrum of the zeolite also exhibits relative intensity characteristics of diffraction peaks as shown in any one of rows of a following table:

| 2θ(°) | relative intensity ($I/I_0 \times 100$) |
|---|---|
| 16.50-17.10 | w-m |
| 48.33-48.93 | w-m. |

In a further preferred embodiment, the X-ray diffraction spectrum of the zeolite also exhibits relative intensity characteristics of diffraction peaks as shown in any one of rows of a following table:

| 2θ(°) | relative intensity ($I/I_0 \times 100$) |
|---|---|
| 13.65-14.25 | w |
| 30.23-30.83 | w |
| 36.67-37.27 | w |
| 43.05-43.65 | w. |

The silicon-aluminum zeolite SCM-36 of the present application has a structure never ever obtained in this field. According to the present application, said SCM-36 zeolite can exist in an uncalcined state (synthetic state) or in a calcined state. When present in a synthetic state, said SCM-36 zeolite typically has a schematic chemical composition as shown by formula "$nSiO_2 \cdot Al_2O_3$·organic structure directing agent·water" or "$nSiO_2 \cdot Al_2O_3 \cdot mMO_x$·organic structure directing agent·water". When present in a calcined state or in a synthetic state, said SCM-36 zeolite can also typically have a schematic chemical composition as shown by formula "$nSiO_2 \cdot Al_2O_3$" or "$nSiO_2 \cdot Al_2O_3 \cdot mMO_x$", wherein n represents the silicon/aluminum ratio of the zeolite and n is ≥5, and m represents the molar ratio of element silicon to element M in the zeolite, and the value of m meets that a total content of said element M in the zeolite is no more than 3 mol % based on an oxide and based on a total amount of Si, Al and element M. In the case of the latter, it is known that a zeolite sometimes comprises a certain amount of water (in particular just after synthesis). However, it is not necessary to determine the amount of water in the present application as the presence of water does not substantially affect the XRD spectrum of the zeolite. In view of this, the schematic chemical composition actually represents the anhydrous chemical composition of the zeolite.

In a preferred embodiment, the specific surface area of the zeolite determined by the BET method is 300-700 $m^2/g$, preferably 300-600 $m^2/g$, more preferably 350-500 $m^2/g$, for example 360-480 $m^2/g$; the external specific surface area is 50-300 $m^2/g$, preferably 80-250 $m^2/g$, and more preferably 100-220 $m^2/g$.

In a preferred embodiment, the total pore volume of the zeolite is 0.20-1.50 $cm^3/g$, preferably 0.40-1.20 $cm^3/g$, more preferably 0.5-1.0 $cm^3/g$; the micropore volume determined by t-plot method is 0.05-0.35 $cm^3/g$, preferably 0.08-0.30 $cm^3/g$, more preferably 0.09-0.25 $cm^3/g$.

In a preferred embodiment, the zeolite has a nano-flake crystal morphology with a crystal thickness of <30 nanometers, preferably 5-25 nanometers, more preferably 7-20 nanometers, for example 10-20 nanometers.

In a preferred embodiment, the total acid content of the zeolite determined by $NH_3$ temperature programmed desorption ($NH_3$-TPD) method is 400-1200 $\mu mol \cdot g^{-1}$, preferably 500-1000 $\mu mol \cdot g^{-1}$, wherein the content of the weak acid, which is defined as an acid with a desorption temperature of 100-250° C., is ≥40%, preferably 45-90%.

In a preferred embodiment, the Lewis acid/Bronsted acid ratio of the zeolite determined by the pyridine adsorption infrared spectrometry is 0.1-3.8, preferably 0.4-3.5.

In a preferred embodiment, the zeolite further comprises at least one element M selected from a group consisting of titanium, boron, zirconium, tin, iron, or a combination thereof.

In a further preferred embodiment, the total content of said element M in the zeolite is no more than 3 mol % based on the oxide and based on the total amount of Si, Al and element M (where the amounts of Si, Al and element M are calculated based on $SiO_2$, $Al_2O_3$ and an oxide form of element M respectively).

In a second aspect, the present application provides a method for manufacturing a silicon-aluminum zeolite, comprising the following steps:

1) crystallizing a mixture containing a silicon source, an aluminum source, an organic structure directing agent (A), an organic structure directing agent (B), an alkali source and water to obtain a zeolite; and
2) optionally, calcining the zeolite obtained in step 1);

wherein the organic structure directing agent (A) is selected from tetramethylammonium compounds, the organic structure directing agent (B) is selected from C6-16 alkylpyridinium compounds, n-octyltrimethylammonium compounds, or a combination thereof.

In a preferred embodiment, in the mixture of step 1), the molar ratio of the silicon source (calculated based on $SiO_2$), the aluminum source (calculated based on $Al_2O_3$), the organic structure directing agent (A), the organic structure directing agent (B), the alkali source and water is 1:(0.01-0.20):(0.05-0.80):(0.05-0.80):(0.05-0.50):(8-80), preferably 1:(0.01-0.10):(0.08-0.65):(0.08-0.65):(0.08-0.45):(10-70), and more preferably 1:(0.02-0.07):(0.10-0.50):(0.10-0.50):(0.10-0.40):(12-60).

In the method of the present application, the crystallization in step 1) can be carried out in any conventionally known manners in the art, for example, a method of mixing the silicon source, the aluminum source, the organic structure directing agent, the alkali source and water in a predetermined ratio, and hydrothermally crystallizing the obtained mixture under crystallization conditions can be exemplified.

In the preferred embodiment, the crystallization temperature of the crystallization in step 1) is 120-200° C., and the crystallization time is 1-15 days; preferably, the crystallization temperature is 130-190° C., and the crystallization time is 2-12 days; more preferably, the crystallization temperature is 140-180° C., and the crystallization time is 3-9 days.

In the method of the present application, after the completion of the crystallization in step 1), the zeolite can be separated from the resulting product mixture as a product through any conventionally known separating methods so as to obtain the silicon-aluminum zeolite SCM-36 of the present application. With respect to the separating methods, for example, a method for filtering, washing and drying the resulting product mixture can be exemplified. Here, the filtering, the washing and the drying can be carried out in any methods conventionally known in the art. Specifically, as an example of the filtering, the resulting product mixture can for example be subjected to a suction filtration; as an example of the washing, deionized water can for example be used for washing; as an example of the drying, the sample can for example be placed in a commercialized blast drying oven for drying. The drying temperature can be 40-150° C., preferably 50-120° C.; the drying time can be 1-30 hours, preferably 2-24 hours. The drying can be carried out under either a normal pressure or a reduced pressure.

In the method of the present application, if desired, the zeolite obtained in step 1) can also be calcined to remove the organic structural directing agent and possible water, so as to obtain the calcined zeolite (also a SCM-36 zeolite of the present application). The calcination can be carried out in any methods conventionally known in the art For example, the calcination temperature generally ranges from 300 to 800° C., preferably 400 to 650° C., and the calcination time generally ranges from 1 to 12 hours, preferably 2 to 10 hours. In addition, said calcination is generally carried out in an oxygen-containing atmosphere, such as air or oxygen atmosphere.

According to the present application, the silicon source and the aluminum source can be various silicon sources and aluminum sources conventionally used for manufacturing silicon-aluminum zeolites, and there is no strict limitation on this in the present application. In a preferred embodiment, the silicon source is selected from a group consisting of silicic acid, silica gel, silica sol, tetraethyl silicate, sodium silicate or a combination thereof; the aluminum source is selected from a group consisting of aluminum hydroxide, aluminum oxide, aluminate, aluminum salt and tetraalkoxy aluminum or a combination thereof.

According to the present application, the alkali source can be various alkali sources conventionally used in the process of manufacturing silicon-aluminum zeolites, and there is no strict limitation on this in the present application. In a preferred embodiment, the alkali source is selected from a group consisting of an inorganic alkali with an alkali metal and/or an alkali earth metal as cation, or a combination thereof. For example, the alkali source can be selected from a group consisting of sodium hydroxide, potassium hydroxide, calcium hydroxide, lithium hydroxide, or a combination thereof.

According to the present application, the organic structure directing agent (A) is selected from tetramethylammonium compounds with $(CH_3)_4N^+$ as cation, for example, tetramethylammonium hydroxide, tetramethylammonium organic acid salts, and tetramethylammonium inorganic acid salts. In a preferred embodiment, the organic structure directing agent (A) is selected from a group consisting of tetramethylammonium hydroxide, tetramethylammonium chloride, tetramethylammonium bromide, tetramethylammonium iodide, or a combination thereof.

According to the present application, the organic structure directing agent (B) is selected from pyridinium compounds with $R(C_5H_5N)^+$ as cation in which R is a $C_{10-16}$ alkyl group, n-octyltrimethylammonium compounds with $C_8H_{17}(CH_3)_3N^+$ as cation, or a combination thereof, for example, $C_{10-16}$ alkylpyridinium hydroxide, $C_{10-16}$ alkylpyridinium organic acid salt, $C_{10-16}$ alkylpyridinium inorganic acid salt, n-octyltrimethylammonium hydroxide, n-octyltrimethylammonium organic acid salt and n-octyltrimethylammonium inorganic acid salt.

In a preferred embodiment, the organic structure directing agent (B) is selected from a group consisting of hexadecylpyridine bromide, tetradecylpyridine bromide, dodecylpyridine bromide, decylpyridine bromide, hexadecylpyridine chloride, tetradecylpyridine chloride, hexadecylpyridine hydroxide, n-octyltrimethylammonium chloride, n-octyltrimethylammonium bromide, n-octyltrimethylammonium hydroxide, or a combination thereof. Further preferably, the organic structure directing agent (B) is selected from a group consisting of hexadecylpyridine bromide, tetradecylpyridine bromide, dodecylpyridine bromide, hexadecylpyridine chloride, hexadecylpyridine hydroxide, n-octyltrimethylammonium chloride, n-octyltrimethylammonium bromide or a combination thereof.

In a preferred embodiment, the mixture in step 1) further comprises at least one source of element M which is selected from a group consisting of titanium, boron, zirconium, tin and iron.

In a further preferred embodiment, the titanium source is selected from a titanium-containing organic metal complex, tetraalkoxy titanium, titanium dioxide, titanium nitrate or a combination thereof; the boron source is selected from boric acid, borate, borax, boron trioxide or a combination thereof; the zirconium source is selected from a zirconium-containing organic metal complex, zirconium salt, zirconium hydroxide, zirconium alcoholate, zirconium dioxide or a combination thereof; the tin source is selected from a tin-containing organic metal complex, tin salt, tin dioxide, or a combination thereof; the iron source is selected from an iron-containing organic metal complex, iron nitrate, iron chloride, iron oxide, or a combination thereof.

In a further preferred embodiment, the molar ratio of the silicon source (calculated based on $SiO_2$) to the source of element M (calculated based on the corresponding oxide) is 1:(0.002-0.10), preferably 1:(0.005-0.05).

In the third aspect, a silicon-aluminum zeolite SCM-36 manufactured according to the method of the present application is provided.

The silicon-aluminum zeolite SCM-36 of the present application can be obtained and used in any physical forms, such as a form of a powder, a particle, or a molded product (such as a strip, a clover, etc.). These physical forms can be obtained in any methods conventionally known in the art without any particular limitations.

In a fourth aspect, the present application provides a zeolite composition comprising the silicon-aluminum zeolite SCM-36 according to the present application or a silicon-aluminum zeolite SCM-36 manufactured according to the method of the present application, and a binder.

The silicon-aluminum zeolite SCM-36 of the present application can be used in combination with additional materials so as to obtain a zeolite composition. Examples of these additional materials may include active materials and inactive materials. Examples of said active materials may include synthetic zeolites, natural zeolites, or other types of zeolites. Said non-active materials (generally referred to as binders) are not strictly limited in the present application. For example, non-active materials can be those conventionally used for manufacturing adsorbents or catalysts, including but not limited to clay, carclazyte, silica, silica gel, alumina, or mixtures thereof. These additional materials can be used alone or in combination in any proportions. The amount of the additional materials can directly refer to conventional amounts in the art without any particular limitations.

According to the present application, the zeolite composition can be presented in any physical forms, such as a form of a powder, a particle, or a molded product (such as a strip, a clover, etc.). These physical forms can be obtained in any methods conventionally known in the art without any particular limitations.

In the fifth aspect, provided is an use of the silicon-aluminum zeolite SCM-36 or the zeolite composition of the present application, or a silicon-aluminum zeolite SCM-36 manufactured according to the method of the present application as an adsorbent, a catalyst, or a catalyst carrier.

The SCM-36 zeolite or the zeolite composition of the present application can be used as an adsorbent, for example, for separating at least one component from a mixture of multiple components in a gas or liquid phase. Based on this, said at least one component can be partially or substantially completely separated from a mixture of various components, for example, specifically by bringing the mixture in contact with the SCM-36 zeolite or the zeolite composition to selectively adsorb the component. As an example of the use as an adsorbent, the use for removing a small amount of water in organic solvents such as isopropanol, isobutanol and isobutyl ketone, and the use for the adsorption and the removal of a small amount of water in natural gas may be mentioned.

In addition, the SCM-36 zeolite or the zeolite composition of the present application can also be used as a catalyst carrier, a catalyst or a catalytic active component thereof directly or after a necessary treatment or conversion (such as ion exchange) conventionally carried out on a zeolite in the art. For example, the SCM-36 zeolite can be used as a catalyst carrier. For instance, the SCM-36 zeolite is loaded with metal Pd to obtain Pd/SCM-36 which can be used as a Pd catalyst for hydrogenation or dehydrogenation reactions, where SCM-36 is a carrier; The SCM-36 can also be used as a bi-functional catalyst, where it serves as a carrier for the metal Pd as well as a solid acid catalysis material which provides an acid site. In addition, reactants (such as hydrocarbons) can be subjected to a predetermined reaction in the presence of a catalyst containing the SCM-36 zeolite or the zeolite composition of the present application, thereby obtaining the target product. Examples of the predetermined reaction may include the reactions of pyrolysis of isopropylbenzene and conversion of methanol to olefins or aromatic hydrocarbons, and the reaction of raw materials of 2,5-dimethylfuran and/or 2,5-hexanedione with ethylene to prepare p-xylene.

In the sixth aspect, the present application provides a catalyst comprising or consisting of the silicon-aluminum zeolite SCM-36 or the zeolite composition of the present application, or a silicon-aluminum zeolite SCM-36 manufactured according to the method of the present application.

In a preferred embodiment, said catalyst is a catalyst suitable for the reactions of pyrolysis of isopropylbenzene and conversion of methanol to olefins or aromatic hydrocarbons, and the reaction of raw materials of 2,5-dimethylfuran and/or 2,5-hexanedione with ethylene to prepare p-xylene.

In a seventh aspect, the present application provides a method for preparing p-xylene, comprising a step of reacting a raw material containing 2,5-dimethylfuran, 2,5-hexanedione or a combination thereof in contact with ethylene in the presence of a catalyst comprising or consisting of the silicon-aluminum zeolite SCM-36 of the present application.

The method for preparing p-xylene in the present application uses the SCM-36 zeolite as a catalyst or a catalyst active component. Under mild reaction conditions, 2,5-dimethylfuran and/or 2,5-hexanedione can be highly-efficiently converted to p-xylene at a very high conversion rate with a very high selectivity of product of p-xylene. Meanwhile, the content of key impurities (such as polyalkylbenzene, 2,5-hexanedione and 2-cyclopentenone) in the obtained product is extremely low, which greatly reduces the separation energy consumption. In addition, the SCM-36 zeolite used as a catalyst in the present application has a high stability and there is no significant change in the performance of the catalyst after four recycles.

In a preferred embodiment, the contact reaction is carried out in the presence of an organic solvent, and the type of organic solvent can be selected within a wide range. Usual organic solvents are all applicable in the present application. Preferably, said organic solvent is selected from a group consisting of n-hexane, n-heptane, γ-valerolactone, tetrahydrofuran, toluene, cyclohexane or a combination thereof. The amount of the organic solvent can be selected within a wide range and can be determined based on the reaction requirements. In a preferred embodiment, the mass ratio of the organic solvent to the raw material is 8-60:1, preferably 10-30:1, which is advantageous in increasing the substrate conversion rate and the selectivity of product of p-xylene, and reducing the content of key impurities in the product.

In the method of the present application, the amount of the catalyst can be selected within a wide range and can be determined based on the reaction requirements specifically. In a preferred embodiment, the mass ratio of the raw material to the catalyst is 0.6-30:1, preferably 1.0-10:1, which is advantageous in increasing the substrate conversion rate and the selectivity of product of p-xylene, and reducing the content of key impurities in the product.

In the method of the present application, the conditions for the contact reaction can be selected within a wide range and can be determined based on the reaction requirements specifically. In a preferred embodiment, the reaction conditions include: the reaction temperature is 160-340° C., preferably 220-270° C.; the reaction time can be determined based on the temperature, for example, the reaction time can be 6-64 hours, preferably 8-48 hours, more preferably 18-40 hours; the reaction pressure is 1-8 MPa, preferably 2-4 MPa.

EXAMPLES

The technical solutions of the present application are further explained in detail with examples. However, the scope of protection of the present application is not limited to these examples.

In the following examples and comparative examples, unless otherwise specified, all the reagents and the raw materials used are commercially available products in analytical purity.

In the following examples and comparative examples which do not specify specific conditions for the experimental methods, the conditions shall be selected according to conventional methods and conditions, or according to the commercial specifications.

In the following examples and comparative examples, the XRD of the zeolite product was measured in such a method: the phase of the sample was analyzed with a Panalytical X PERPRO X-ray powder diffractometer having a CuKα ray source (λ=1.54 Å), a nickel filter, 2θ scanning range 2-50°, an operating voltage 40 KV, a current 40 mA, and a scanning rate 10°/min.

In the following examples and comparative examples, the inductively coupled plasma atomic emission spectrometer (ICP) had a model of Varian 725-ES, and the analysis sample was dissolved with hydrofluoric acid to detect and obtain the contents of elements in the sample.

In the following examples and comparative examples, $NH_3$ temperature programmed desorption ($NH_3$-TPD) experiment was conducted on a TPD/TPR Altamira AMI-3300 instrument, and the total acid amount was calculated by a peak fitting of the resulting spectrum. The acid corresponding to the desorption temperature of 100-250° C. was defined as weak acid, and the proportion of the weak acid was calculated accordingly.

In the following examples and comparative examples, the scanning electron microscopy images were tested using a field emission scanning electron microscopy with model Hitachi S-4800II of Japanese Hitachi Company under a test voltage of 15 KV. Transmission electron microscope of G2F30 from Dutch FEI with a working voltage of 300 kV was used. The zeolite was observed at a magnification of 100,000 times, and the thicknesses of all crystals in a randomly selected observation field were measured. After repeating the operation for 5 times, the average value of the 5 measurements was taken as the average thickness of the crystals.

In the following examples and comparative examples, the Py-FTIR spectrogram was tested with a Thermo Nicolet 5700FT-IR spectrometer.

Example I-1

24.73 g of deionized water, 6.89 g of sodium hydroxide solution (comprising 10 wt. % of NaOH), 5.35 g of the organic structure directing agent (A): tetramethylammonium hydroxide (comprising 25 wt. % of TMAOH), 3.05 g of the organic structure directing agent (B): n-octyltrimethylammonium chloride, 1.234 g of sodium metaaluminate (comprising 40.5 wt. % of $Al_2O_3$ and 30.6 wt. % of $Na_2O$), 14.72 g of silica sol (comprising 40 wt. % of $SiO_2$) were mixed evenly to prepare a mixture. The material ratios (molar ratio) of the reactants are:

$$Al_2O_3/SiO_2 = 0.05$$

$$\text{Tetramethylammonium hydroxide } (A)/SiO_2 = 0.15$$

$$\text{n-octyltrimethylammonium chloride } (B)/SiO_2 = 0.15$$

$$NaOH/SiO_2 = 0.30$$

$$H_2O/SiO_2 = 25;$$

after evenly mixing, the mixture was added in a stainless steel reactor and crystallized at 160° C. for 6 days. Upon completion of the crystallization, the product was filtered, washed, dried in an oven at 110° C. for 12 hours, and calcined in air at 550° C. for 6 hours to obtain a zeolite.

Figure 2:
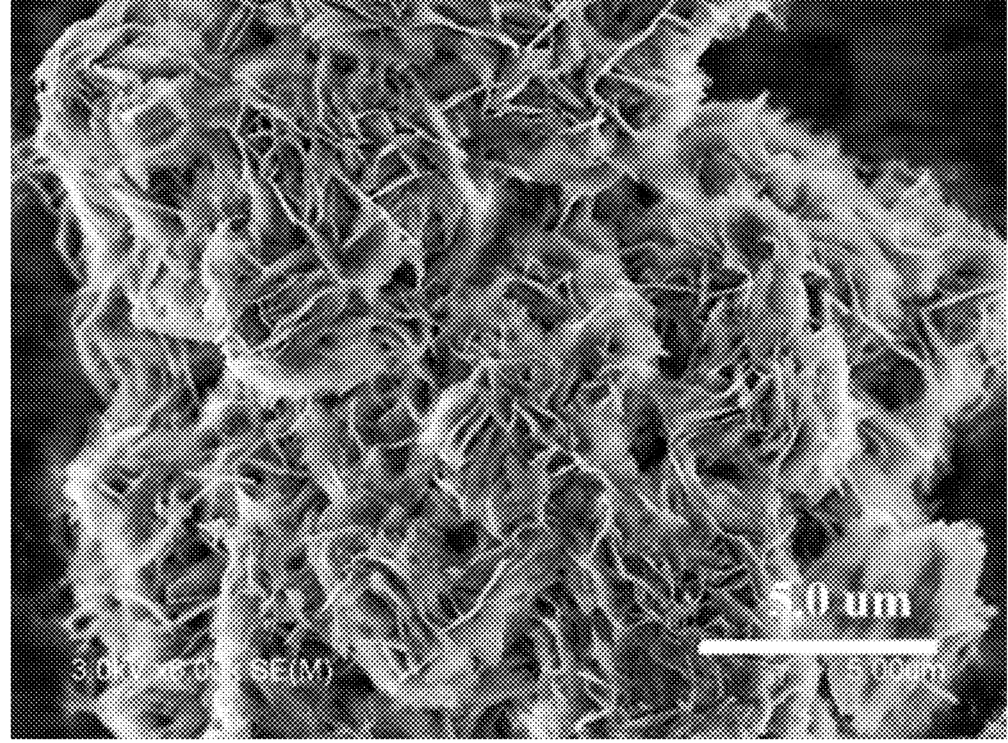
FIG. 2 illustrates the scanning electron microscopy (SEM) image of the zeolite obtained in Example I-1.
Figure 3:
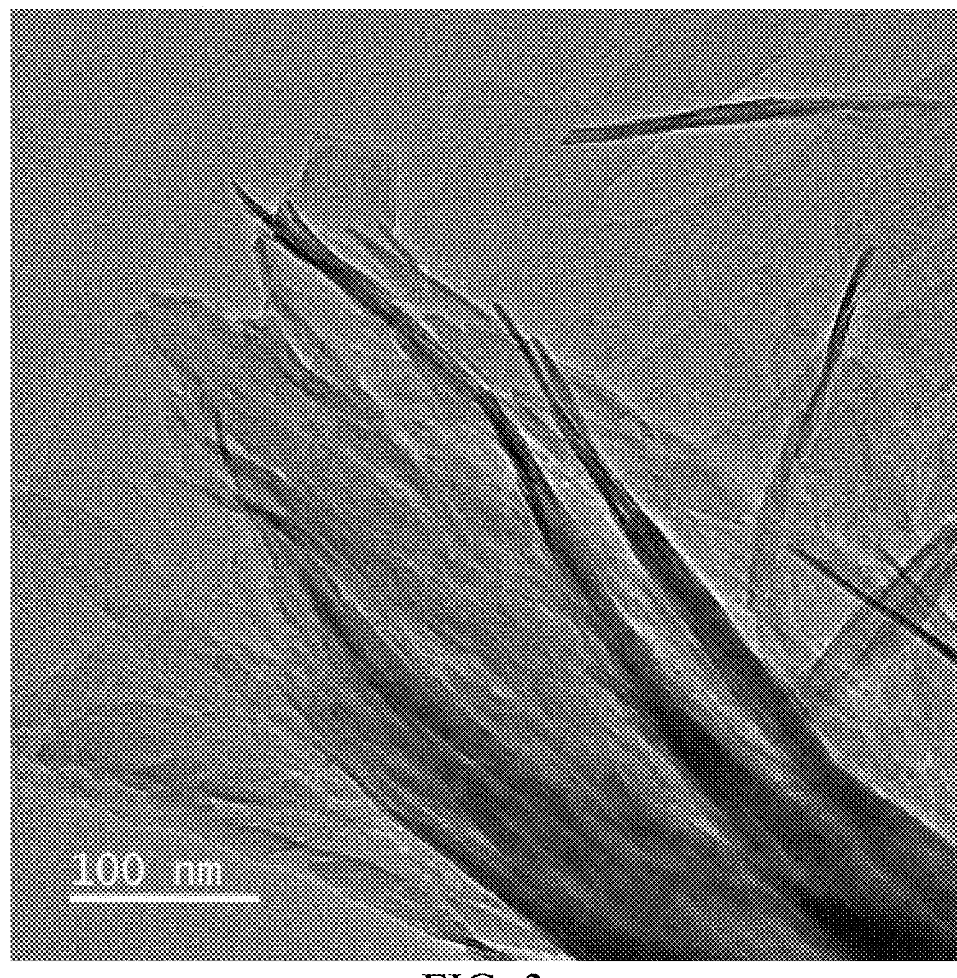
FIG. 3 illustrates the transmission electron microscopy (TEM) image of the zeolite obtained in Example I-1.

The XRD spectrum data of the dried sample are shown in Table I-1 and FIG. 1, the SEM image of the sample is illustrated in FIG. 2, and the TEM image is illustrated in FIG. 3.

TABLE I-1

XRD spectrum data of the resulting zeolite in Example I-1

| 2θ(°) | interplanar spacing (Å) | relative intensity ($I/I_0 \times 100$) |
|---|---|---|
| 9.09 | 9.721 | 45 |
| 12.74 | 6.944 | 41 |
| 13.95 | 6.341 | 14 |
| 16.92 | 5.236 | 18 |
| 19.12 | 4.637 | 46 |
| 23.68 | 3.754 | 37 |
| 24.37 | 3.651 | 37 |
| 25.81 | 3.449 | 100 |
| 30.53 | 2.926 | 8 |
| 43.22 | 2.102 | 7 |
| 48.62 | 1.871 | 11 |

The resulting calcined product has a specific surface area of 380 $m^2/g$, an external specific surface area of 170 $m^2/g$, a total pore volume of 0.92 $cm^3/g$, and a microporous volume of 0.10 $cm^3/g$. The sample has a nano-flake morphology and a crystal thickness of approximately 15 nanometers.

The calcined sample has a $SiO_2/Al_2O_3$=21.6 (molar ratio) measured using the inductively coupled plasma atomic emission spectroscopy (ICP).

Figure 4:
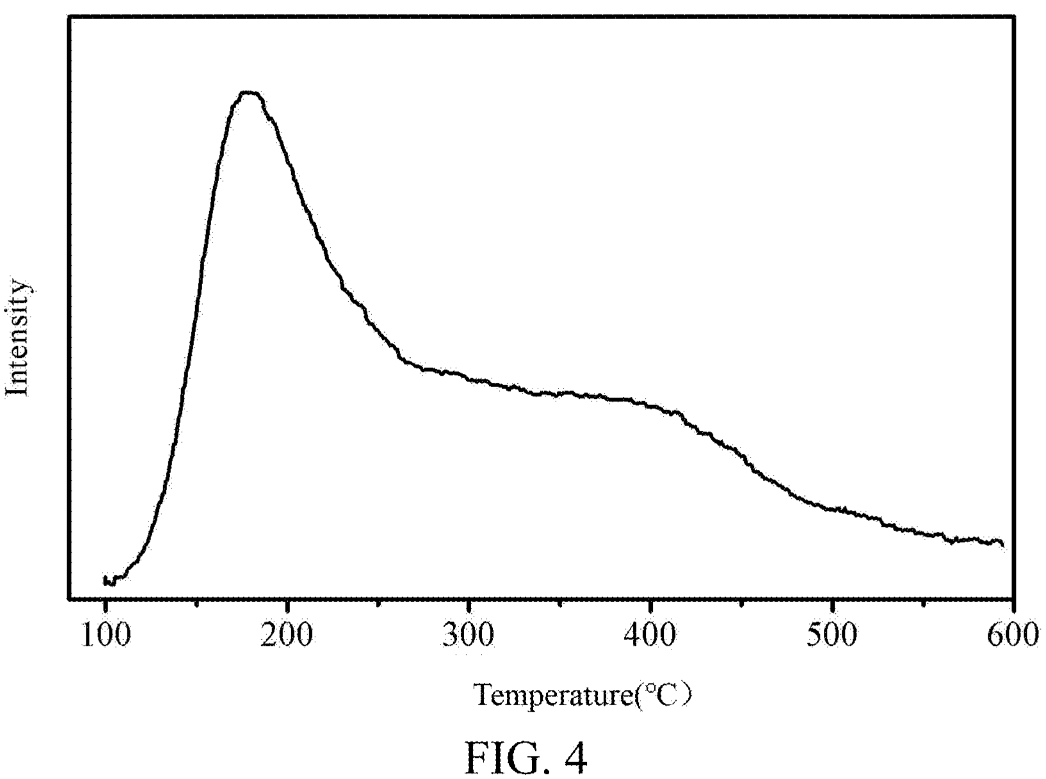
FIG. 4 illustrates the ammonia temperature programmed desorption ($NH_3$-TPD) spectrum of the zeolite obtained in Example I-1.
Figure 5:
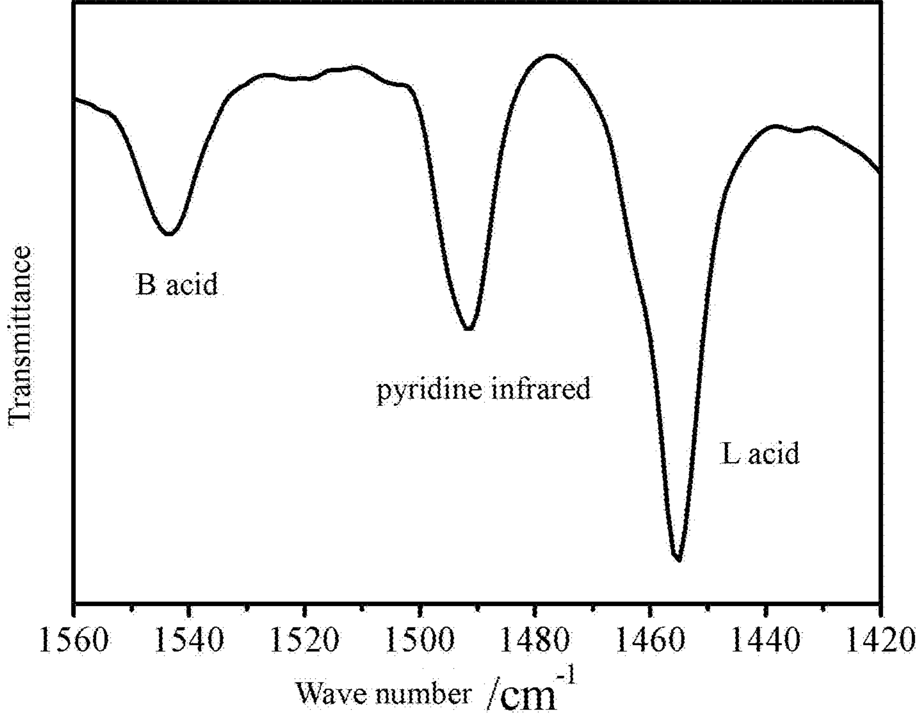
FIG. 5 illustrates the pyridine adsorption infrared (Py-FTIR) spectrum of the zeolite obtained in Example I-1.

The ammonia temperature programmed desorption ($NH_3$-TPD) spectrum of the resulting sample is shown in FIG. 4. A total acid content resulted therefrom is 782 $\mu mol \cdot g^{-1}$ with a weak acid content of 63%. The infrared spectrum of pyridine adsorption is shown in FIG. 5, and the Lewis/Bronsted acid ratio is analyzed and measured to be 2.2.

Example I-2

The test was carried out by reference to Example I-1, except that the used reactants and material ratios (molar ratio) were:

$$Al_2O_3/SiO_2 = 0.067$$

$$\text{Tetramethylammonium hydroxide } (A)/SiO_2 = 0.15$$

$$\text{n-octyltrimethylammonium chloride } (B)/SiO_2 = 0.20$$

$$NaOH/SiO_2 = 0.30$$

$$H_2O/SiO_2 = 20;$$

after evenly mixing, the mixture was added in a stainless steel reactor and crystallized at 160° C. for 5 days. Upon completion of the crystallization, the product was filtered, washed, dried in an oven at 100° C. for 16 hours, and calcined in air at 550° C. for 8 hours to obtain a zeolite.

Figure 6:
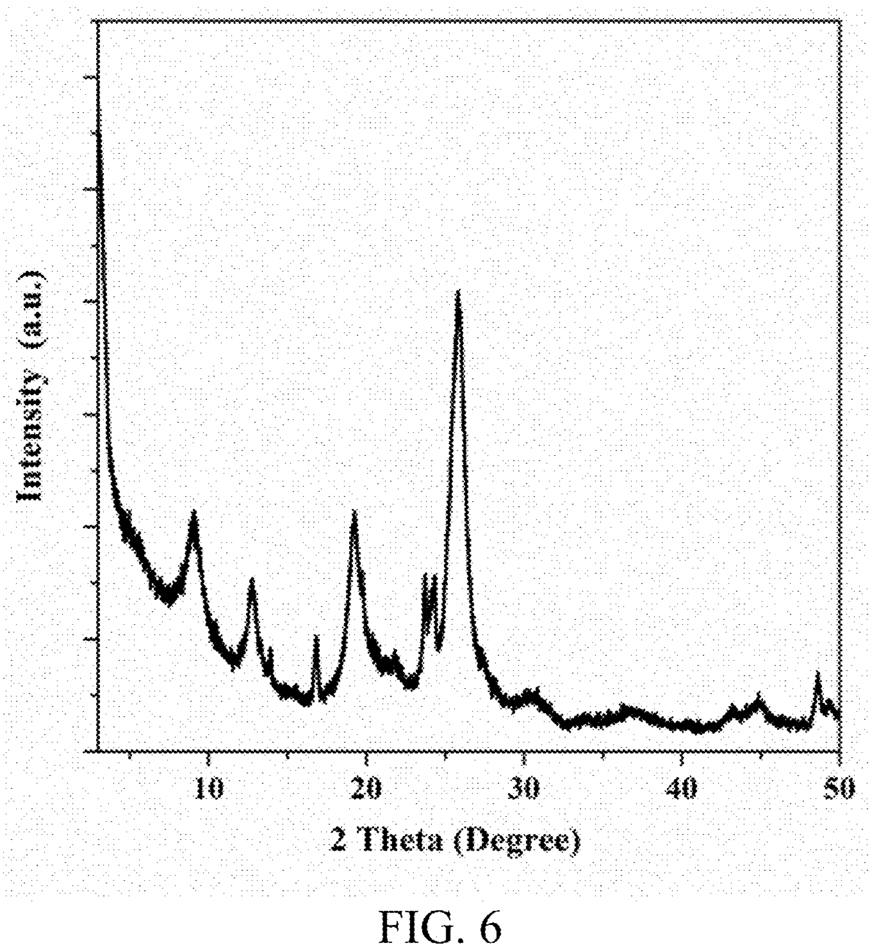
FIG. 6 illustrates the XRD spectrum of the zeolite obtained in Example I-2.

The XRD spectrum data of the dried sample are shown in Table I-2 and FIG. 6, and the SEM image of the sample is similar to that illustrated in FIG. 2.

TABLE I-2

XRD spectrum data of the resulting zeolite in Example I-2

| 2θ(°) | interplanar spacing (Å) | relative intensity ($I/I_0 \times 100$) |
|---|---|---|
| 9.48 | 9.192 | 62 |
| 12.96 | 6.823 | 71 |
| 14.12 | 6.265 | 15 |
| 16.78 | 5.280 | 5 |
| 19.34 | 4.585 | 47 |
| 23.89 | 3.722 | 39 |
| 24.37 | 3.645 | 38 |
| 26.15 | 3.386 | 100 |
| 43.33 | 2.092 | 5 |
| 48.88 | 1.851 | 8 |

The resulting calcined product has a specific surface area of 392 $m^2/g$, an external specific surface area of 166 $m^2/g$, a total pore volume of 0.73 $cm^3/g$, and a microporous volume of 0.10 $cm^3/g$. The sample has a nano-flake morphology and a crystal thickness of approximately 12 nanometers.

The calcined sample has a $SiO_2/Al_2O_3$=15.6 (molar ratio) measured using the inductively coupled plasma atomic emission spectroscopy (ICP).

The ammonia temperature programmed desorption ($NH_3$-TPD) spectrum of the resulting sample is similar to that illustrated in FIG. 4. A total acid content resulted therefrom is 827 $\mu mol \cdot g^{-1}$ with a weak acid content of 61%. The infrared spectrum of pyridine adsorption is similar to that illustrated in FIG. 5, and the Lewis/Bronsted acid ratio is analyzed and measured to be 2.5.

Example I-3

The test was carried out by reference to Example I-1, except that the used reactants and material ratios (molar ratio) were:

$$Al_2O_3/SiO_2 = 0.04$$

$$\text{Tetramethylammonium chloride } (A)/SiO_2 = 0.20$$

$$\text{n-octyltrimethylammonium chloride } (B)/SiO_2 = 0.15$$

$$NaOH/SiO_2 = 0.25$$

$$H_2O/SiO_2 = 35;$$

after evenly mixing, the mixture was added in a stainless steel reactor and crystallized at 155° C. for 7 days. Upon completion of the crystallization, the product was filtered, washed, dried in an oven at 80° C. for 16 hours, and calcined in air at 500° C. for 10 hours to obtain a zeolite.

Figure 7:
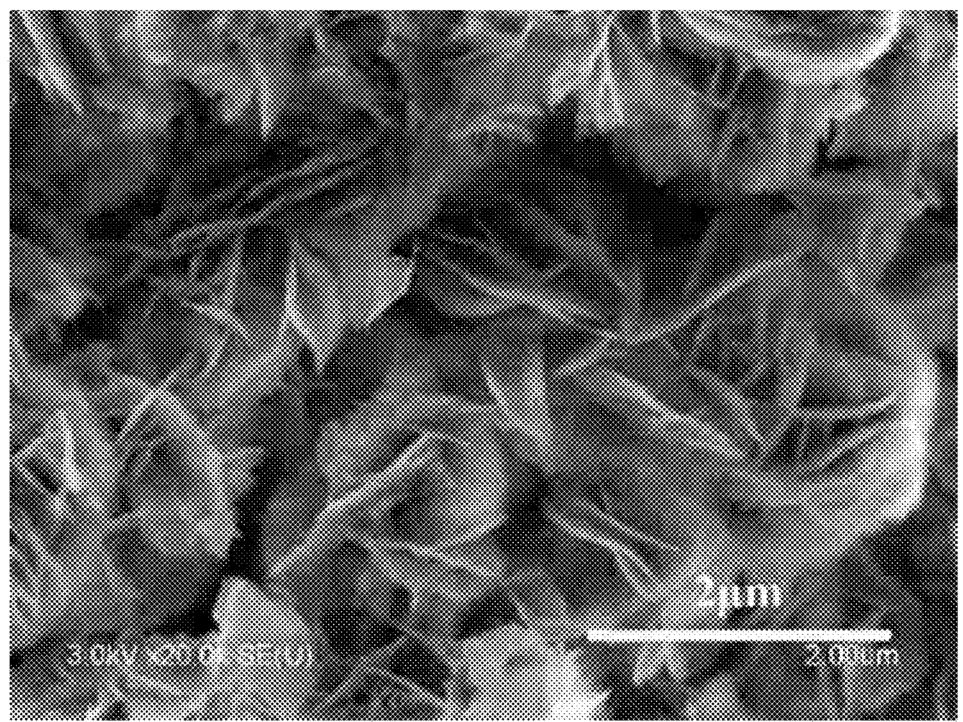
FIG. 7 illustrates the SEM image of the zeolite obtained in Example I-3.

The XRD spectrum data of the dried sample are shown in Table I-3, and the SEM image of the sample is illustrated in FIG. 7.

TABLE I-3

XRD spectrum data of the resulting zeolite in Example I-3

| 2θ(°) | interplanar spacing (Å) | relative intensity ($I/I_0 \times 100$) |
|---|---|---|
| 9.40 | 9.329 | 60 |
| 12.87 | 6.873 | 64 |
| 14.10 | 6.275 | 19 |
| 16.80 | 5.271 | 28 |
| 19.30 | 4.593 | 45 |
| 23.79 | 3.733 | 38 |
| 24.32 | 3.649 | 34 |
| 26.19 | 3.394 | 100 |
| 30.56 | 2.917 | 7 |
| 36.82 | 2.408 | 5 |
| 48.84 | 1.846 | 8 |

The resulting calcined product has a specific surface area of 388 $m^2/g$, an external specific surface area of 162 $m^2/g$, a total pore volume of 0.75 $cm^3/g$, and a microporous volume of 0.10 $cm^3/g$. The sample has a nano-flake morphology and a crystal thickness of approximately 13 nanometers.

The calcined sample has a $SiO_2/Al_2O_3$=26.1 (molar ratio) measured using the inductively coupled plasma atomic emission spectroscopy (ICP).

The ammonia temperature programmed desorption ($NH_3$-TPD) spectrum of the resulting sample is similar to that illustrated in FIG. 4. A total acid content resulted therefrom is 674 $\mu mol \cdot g^{-1}$ with a weak acid content of 68%. The infrared spectrum of pyridine adsorption is similar to that illustrated in FIG. 5, and the Lewis/Bronsted acid ratio is analyzed and measured to be 1.1.

Example I-4

The test was carried out by reference to Example I-1, except that the used reactants and material ratios (molar ratio) were:

$$Al_2O_3/SiO_2 = 0.045$$

$$\text{Tetramethylammonium hydroxide } (A)/SiO_2 = 0.25$$

$$\text{n-octyltrimethylammonium chloride } (B)/SiO_2 = 0.15$$

$$NaOH/SiO_2 = 0.20$$

$$H_2O/SiO_2 = 45;$$

after evenly mixing, the mixture was added in a stainless steel reactor and crystallized at 165° C. for 4 days. Upon completion of the crystallization, the product was filtered, washed, dried in an oven at 60° C. for 24 hours, and calcined in air at 600° C. for 4 hours to obtain a zeolite.

The XRD spectrum data of the dried sample are shown in Table I-4, and the SEM image of the sample is similar to that illustrated in FIG. 2.

TABLE I-4

XRD spectrum data of the resulting zeolite in Example I-4

| 2θ(°) | interplanar spacing (Å) | relative intensity ($I/I_0 \times 100$) |
|---|---|---|
| 9.24 | 9.583 | 56 |
| 12.71 | 6.967 | 50 |
| 14.07 | 6.294 | 27 |
| 16.85 | 5.255 | 22 |
| 19.22 | 4.607 | 41 |
| 23.59 | 3.754 | 37 |
| 24.22 | 3.665 | 37 |
| 26.15 | 3.386 | 100 |
| 30.71 | 2.883 | 6 |
| 36.88 | 2.401 | 5 |
| 48.69 | 1.819 | 7 |

The resulting calcined product has a specific surface area of 377 $m^2/g$, an external specific surface area of 158 $m^2/g$, a total pore volume of 0.74 $cm^3/g$, and a microporous volume of 0.11 $cm^3/g$. The sample has a nano-flake morphology and a crystal thickness of approximately 11 nanometers.

The calcined sample has a $SiO_2/Al_2O_3$=22.3 (molar ratio) measured using the inductively coupled plasma atomic emission spectroscopy (ICP).

The ammonia temperature programmed desorption ($NH_3$-TPD) spectrum of the resulting sample is similar to that illustrated in FIG. 4. A total acid content resulted therefrom is 835 $\mu mol \cdot g^{-1}$ with a weak acid content of 64%. The infrared spectrum of pyridine adsorption is similar to that illustrated in FIG. 5, and the Lewis/Bronsted acid ratio is analyzed and measured to be 2.8.

Example I-5

The test was carried out by reference to Example I-1, except that the used reactants and material ratios (molar ratio) were:

$$Al_2O_3/SiO_2 = 0.017$$

$$\text{Tetramethylammonium hydroxide } (A)/SiO_2 = 0.20$$

$$\text{n-octyltrimethylammonium chloride } (B)/SiO_2 = 0.25$$

-continued $$NaOH/SiO_2 = 0.20$$

$$H_2O/SiO_2 = 30;$$

after evenly mixing, the mixture was added in a stainless steel reactor and crystallized at 155° C. for 8 days. Upon completion of the crystallization, the product was filtered, washed, dried in an oven at 120° C. for 6 hours, and calcined in air at 550° C. for 8 hours to obtain a zeolite.

The XRD spectrum data of the dried sample are shown in Table I-5, and the SEM image of the sample is similar to that illustrated in FIG. 2.

TABLE I-5

XRD spectrum data of the resulting zeolite in Example I-5

| 2θ(°) | interplanar spacing (Å) | relative intensity ($I/I_0 \times 100$) |
|---|---|---|
| 9.35 | 9.407 | 55 |
| 12.83 | 6.901 | 54 |
| 17.00 | 5.123 | 25 |
| 19.26 | 4.606 | 54 |
| 23.74 | 3.743 | 38 |
| 24.22 | 3.665 | 36 |
| 26.07 | 3.412 | 100 |
| 30.61 | 2.916 | 7 |
| 36.90 | 2.419 | 4 |
| 43.49 | 2.066 | 3 |
| 48.78 | 1.857 | 8 |

The resulting calcined product has a specific surface area of 372 $m^2/g$, an external specific surface area of 149 $m^2/g$, a total pore volume of 0.74 $cm^3/g$, and a microporous volume of 0.09 $cm^3/g$. The sample has a nano-flake morphology and a crystal thickness of approximately 12 nanometers.

The calcined sample has a $SiO_2/Al_2O_3$=61.5 (molar ratio) measured using the inductively coupled plasma atomic emission spectroscopy (ICP).

The ammonia temperature programmed desorption ($NH_3$-TPD) spectrum of the resulting sample is similar to that illustrated in FIG. 4. A total acid content resulted therefrom is 621 $\mu mol \cdot g^{-1}$ with a weak acid content of 56%. The infrared spectrum of pyridine adsorption is similar to that illustrated in FIG. 5, and the Lewis/Bronsted acid ratio is analyzed and measured to be 1.0.

Example I-6

The test was carried out by reference to Example I-1, except that the used reactants and material ratios (molar ratio) were:

$$Al_2O_3/SiO_2 = 0.03$$

$$\text{Tetramethylammonium iodide } (A)/SiO_2 = 0.20$$

$$\text{n-octyltrimethylammonium chloride } (B)/SiO_2 = 0.20$$

$$NaOH/SiO_2 = 0.25$$

$$H_2O/SiO_2 = 35;$$

after evenly mixing, the mixture was added in a stainless steel reactor and crystallized at 170° C. for 5 days. Upon completion of the crystallization, the product was filtered, washed, dried in an oven at 100° C. for 12 hours, and calcined in air at 500° C. for 10 hours to obtain a zeolite.

The XRD spectrum data of the dried sample are shown in Table I-6, and the SEM image of the sample is similar to that illustrated in FIG. 2.

TABLE I-6

XRD spectrum data of the resulting zeolite in Example I-6

| 2θ(°) | interplanar spacing (Å) | relative intensity ($I/I_0 \times 100$) |
|---|---|---|
| 9.40 | 9.329 | 60 |
| 12.87 | 6.873 | 64 |
| 14.10 | 6.275 | 19 |
| 16.92 | 5.236 | 28 |
| 19.30 | 4.593 | 45 |
| 23.79 | 3.733 | 38 |
| 24.32 | 3.649 | 36 |
| 26.19 | 3.394 | 100 |
| 30.56 | 2.917 | 7 |
| 36.82 | 2.408 | 5 |
| 48.84 | 1.846 | 8 |

The resulting calcined product has a specific surface area of 362 $m^2/g$, an external specific surface area of 149 $m^2/g$, a total pore volume of 0.67 $cm^3/g$, and a microporous volume of 0.10 $cm^3/g$. The sample has a nano-flake morphology and a crystal thickness of approximately 12 nanometers.

The calcined sample has a $SiO_2/Al_2O_3$=34.5 (molar ratio) measured using the inductively coupled plasma atomic emission spectroscopy (ICP).

The ammonia temperature programmed desorption ($NH_3$-TPD) spectrum of the resulting sample is similar to that illustrated in FIG. 4. A total acid content resulted therefrom is 643 $\mu mol \cdot g^{-1}$ with a weak acid content of 66%. The infrared spectrum of pyridine adsorption is similar to that illustrated in FIG. 5, and the Lewis/Bronsted acid ratio is analyzed and measured to be 2.1.

Example I-7

The test was carried out by reference to Example I-1, except that the used reactants and material ratios (molar ratio) were:

$$Al_2O_3/SiO_2 = 0.05$$

$$\text{Tetramethylammonium hydroxide } (A)/SiO_2 = 0.15$$

$$\text{Tetradecylpyridine bromide } (B)/SiO_2 = 0.15$$

$$NaOH/SiO_2 = 0.30$$

$$H_2O/SiO_2 = 35;$$

after evenly mixing, the mixture was added in a stainless steel reactor and crystallized at 160° C. for 7 days. Upon completion of the crystallization, the product was filtered, washed, dried in an oven at 110° C. for 6 hours, and calcined in air at 550° C. for 6 hours to obtain a zeolite.

The XRD spectrum data of the dried sample are shown in Table I-7, and the SEM image of the sample is similar to that illustrated in FIG. 2.

TABLE I-7

XRD spectrum data of the resulting zeolite in Example I-7

| 2θ(°) | interplanar spacing (Å) | relative intensity ($I/I_0 \times 100$) |
|---|---|---|
| 9.38 | 9.376 | 58 |
| 12.85 | 6.890 | 61 |
| 16.95 | 5.168 | 26 |
| 19.28 | 4.601 | 47 |
| 23.77 | 3.739 | 38 |
| 24.28 | 3.659 | 36 |
| 26.14 | 3.405 | 100 |
| 30.58 | 2.916 | 6 |
| 36.85 | 2.414 | 4 |
| 43.44 | 2.083 | 4 |
| 48.82 | 1.853 | 7 |

The resulting calcined product has a specific surface area of 378 $m^2/g$, an external specific surface area of 156 $m^2/g$, a total pore volume of 0.77 $cm^3/g$, and a microporous volume of 0.11 $cm^3/g$. The sample has a nano-flake morphology and a crystal thickness of approximately 13 nanometers.

The calcined sample has a $SiO_2/Al_2O_3$=21.1 (molar ratio) measured using the inductively coupled plasma atomic emission spectroscopy (ICP).

The ammonia temperature programmed desorption ($NH_3$-TPD) spectrum of the resulting sample is similar to that illustrated in FIG. 4. A total acid content resulted therefrom is 815 $\mu mol \cdot g^{-1}$ with a weak acid content of 68%. The infrared spectrum of pyridine adsorption is similar to that illustrated in FIG. 5, and the Lewis/Bronsted acid ratio is analyzed and measured to be 1.7.

Example I-8

The test was carried out by reference to Example I-1, except that hexadecylpyridine bromide was used as the organic structure directing agent (B), and the material ratios (molar ratios) of the reactants were:

$$Al_2O_3/SiO_2 = 0.045$$

$$\text{Tetramethylammonium hydroxide } (A)/SiO_2 = 0.15$$

$$\text{Hexadecylpyridine bromide } (B)/SiO_2 = 0.20$$

$$NaOH/SiO_2 = 0.25$$

$$H_2O/SiO_2 = 30;$$

after evenly mixing, the mixture was added in a stainless steel reactor and crystallized at 160° C. for 6 days. Upon completion of the crystallization, the product was filtered, washed, dried in an oven at 90° C. for 12 hours, and calcined in air at 550° C. for 6 hours to obtain a zeolite.

The XRD spectrum data of the dried sample are shown in Table I-8, and the SEM image of the sample is similar to that illustrated in FIG. 2.

TABLE I-8

| XRD spectrum data of the resulting zeolite in Example I-8 | | |
|---|---|---|
| 2θ(°) | interplanar spacing (Å) | relative intensity ($I/I_0 \times 100$) |
| 9.29 | 9.457 | 53 |
| 12.85 | 6.884 | 55 |
| 14.04 | 6.303 | 15 |
| 16.85 | 5.258 | 12 |
| 19.23 | 4.611 | 47 |
| 23.79 | 3.738 | 37 |
| 24.22 | 3.672 | 36 |
| 26.01 | 3.424 | 100 |
| 30.51 | 2.931 | 8 |
| 43.28 | 2.097 | 6 |
| 48.77 | 1.866 | 10 |

The resulting calcined product has a specific surface area of 394 $m^2/g$, an external specific surface area of 171 $m^2/g$, a total pore volume of 0.68 $cm^3/g$, and a microporous volume of 0.12 $cm^3/g$. The sample has a nano-flake morphology and a crystal thickness of approximately 12 nanometers.

The calcined sample has a $SiO_2/Al_2O_3$=22.8 (molar ratio) measured using the inductively coupled plasma atomic emission spectroscopy (ICP).

The ammonia temperature programmed desorption ($NH_3$-TPD) spectrum of the resulting sample is similar to that illustrated in FIG. 4. A total acid content resulted therefrom is 849 μmol·$g^{-1}$ with a weak acid content of 59%. The infrared spectrum of pyridine adsorption is similar to that illustrated in FIG. 5, and the Lewis/Bronsted acid ratio is analyzed and measured to be 2.3.

Example I-9

The test was carried out by reference to Example I-8, except that the used reactants and material ratios (molar ratio) were:

$$Al_2O_3/SiO_2 = 0.068$$

$$\text{Tetramethylammonium hydroxide } (A)/SiO_2 = 0.20$$

$$\text{Hexadecylpyridine bromide } (B)/SiO_2 = 0.15$$

$$NaOH/SiO_2 = 0.30$$

$$H_2O/SiO_2 = 40;$$

after evenly mixing, the mixture was added in a stainless steel reactor and crystallized at 160° C. for 6 days. Upon completion of the crystallization, the product was filtered, washed, dried in an oven at 80° C. for 16 hours, and calcined in air at 550° C. for 6 hours to obtain a zeolite.

The XRD spectrum data of the dried sample are shown in Table I-9, and the SEM image of the sample is similar to that illustrated in FIG. 2.

TABLE I-9

| XRD spectrum data of the resulting zeolite in Example I-9 | | |
|---|---|---|
| 2θ(°) | interplanar spacing (Å) | relative intensity ($I/I_0 \times 100$) |
| 9.36 | 9.388 | 59 |
| 12.84 | 6.895 | 61 |
| 14.10 | 6.280 | 21 |
| 16.61 | 5.332 | 37 |
| 19.28 | 4.596 | 44 |
| 23.74 | 3.738 | 36 |
| 24.30 | 3.651 | 35 |
| 26.18 | 3.392 | 100 |
| 30.60 | 2.909 | 7 |
| 36.91 | 2.396 | 5 |
| 48.81 | 1.840 | 8 |

The resulting calcined product has a specific surface area of 372 $m^2/g$, an external specific surface area of 144 $m^2/g$, a total pore volume of 0.65 $cm^3/g$, and a microporous volume of 0.11 $cm^3/g$. The sample has a nano-flake morphology and a crystal thickness of approximately 15 nanometers.

The calcined sample has a $SiO_2/Al_2O_3$=14.5 (molar ratio) measured using the inductively coupled plasma atomic emission spectroscopy (ICP).

The ammonia temperature programmed desorption ($NH_3$-TPD) spectrum of the resulting sample is similar to that illustrated in FIG. 4. A total acid content resulted therefrom is 896 μmol·$g^{-1}$ with a weak acid content of 82%. The infrared spectrum of pyridine adsorption is similar to that illustrated in FIG. 5, and the Lewis/Bronsted acid ratio is analyzed and measured to be 3.0

Example I-10

The test was carried out by reference to Example I-1, except that the used reactants and material ratios (molar ratio) were:

$$Al_2O_3/SiO_2 = 0.05$$

$$TiO_2/SiO_2 = 0.01$$

$$\text{Tetramethylammonium hydroxide } (A)/SiO_2 = 0.15$$

$$\text{n-octyltrimethylammonium chloride } (B)/SiO_2 = 0.20$$

$$NaOH/SiO_2 = 0.25$$

$$H_2O/SiO_2 = 35;$$

after evenly mixing, the mixture was added in a stainless steel reactor and crystallized at 160° C. for 7 days. Upon completion of the crystallization, the product was filtered, washed, dried in an oven at 100° C. for 10 hours, and calcined in air at 550° C. for 6 hours to obtain a zeolite.

The XRD spectrum data of the dried sample are shown in Table I-10, and the SEM image of the sample is similar to that illustrated in FIG. 2.

TABLE I-10

| XRD spectrum data of the resulting zeolite in Example I-10 | | |
|---|---|---|
| 2θ(°) | interplanar spacing (Å) | \relative intensity ($I/I_0 \times 100$) |
| 9.34 | 9.377 | 56 |
| 12.88 | 6.865 | 59 |
| 14.06 | 6.292 | 15 |
| 16.83 | 5.265 | 10 |

TABLE I-10-continued

XRD spectrum data of the resulting zeolite in Example I-10

| 2θ(°) | interplanar spacing (Å) | \relative intensity ($I/I_0 \times 100$) |
|---|---|---|
| 19.26 | 4.603 | 47 |
| 23.82 | 3.733 | 39 |
| 24.37 | 3.647 | 37 |
| 26.07 | 3.416 | 100 |
| 30.50 | 2.932 | 8 |
| 43.29 | 2.091 | 6 |
| 48.82 | 1.864 | 9 |

The resulting calcined product has a specific surface area of 364 $m^2/g$, an external specific surface area of 146 $m^2/g$, a total pore volume of 0.71 $cm^3/g$, and a microporous volume of 0.12 $cm^3/g$. The sample has a nano-flake morphology and a crystal thickness of approximately 18 nanometers.

The calcined sample has a $SiO_2/Al_2O_3$=21.2 (molar ratio) and a $SiO_2/TiO_2$=106.2 (molar ratio) measured using the inductively coupled plasma atomic emission spectroscopy (ICP).

The ammonia temperature programmed desorption ($NH_3$-TPD) spectrum of the resulting sample is similar to that illustrated in FIG. 4. A total acid content resulted therefrom is 795 $\mu mol \cdot g^{-1}$ with a weak acid content of 60%. The infrared spectrum of pyridine adsorption is similar to that illustrated in FIG. 5, and the Lewis/Bronsted acid ratio is analyzed and measured to be 1.6.

Example I-11

The test was carried out by reference to Example I-1, except that the used reactants and material ratios (molar ratio) were:

$$Al_2O_3/SiO_2 = 0.065$$

$$B_2O_3/SiO_2 = 0.012$$

$$\text{Tetramethylammonium hydroxide } (A)/SiO_2 = 0.20$$

$$\text{n-octyltrimethylammonium chloride } (B)/SiO_2 = 0.15$$

$$NaOH/SiO_2 = 0.30$$

$$H_2O/SiO_2 = 40;$$

after evenly mixing, the mixture was added in a stainless steel reactor and crystallized at 155° C. for 7 days. Upon completion of the crystallization, the product was filtered, washed, dried in an oven at 80° C. for 8 hours, and calcined in air at 550° C. for 6 hours to obtain a zeolite.

The XRD spectrum data of the dried sample are shown in Table I-11, and the SEM image of the sample is similar to that illustrated in FIG. 2.

TABLE I-11

XRD spectrum data of the resulting zeolite in Example I-11

| 2θ(°) | interplanar spacing (Å) | relative intensity ($I/I_0 \times 100$) |
|---|---|---|
| 9.33 | 9.407 | 56 |
| 12.86 | 6.881 | 58 |
| 14.07 | 6.292 | 17 |
| 16.76 | 5.285 | 20 |
| 19.26 | 4.603 | 46 |
| 23.78 | 3.736 | 36 |
| 24.30 | 3.657 | 38 |
| 26.09 | 3.411 | 100 |
| 30.54 | 2.924 | 8 |
| 36.88 | 2.407 | 5 |
| 48.80 | 1.857 | 9 |

The resulting calcined product has a specific surface area of 385 $m^2/g$, an external specific surface area of 152 $m^2/g$, a total pore volume of 0.63 $cm^3/g$, and a microporous volume of 0.09 $cm^3/g$. The sample has a nano-flake morphology and a crystal thickness of approximately 20 nanometers.

The calcined sample has a $SiO_2/Al_2O_3$=15.9 (molar ratio) and a $SiO_2/B_2O_3$=96.3 (molar ratio) measured using the inductively coupled plasma atomic emission spectroscopy (ICP).

The ammonia temperature programmed desorption ($NH_3$-TPD) spectrum of the resulting sample is similar to that illustrated in FIG. 4. A total acid content resulted therefrom is 860 $\mu mol \cdot g^{-1}$ with a weak acid content of 74%. The infrared spectrum of pyridine adsorption is similar to that illustrated in FIG. 5, and the Lewis/Bronsted acid ratio is analyzed and measured to be 3.2.

Example I-12

The test was carried out by reference to Example I-7, except that the used reactants and material ratios (molar ratio) were:

$$Al_2O_3/SiO_2 = 0.035$$

$$ZrO_2/SiO_2 = 0.008$$

$$\text{Tetramethylammonium hydroxide } (A)/SiO_2 = 0.20$$

$$\text{Dodecylpyridine bromide } (B)/SiO_2 = 0.20$$

$$NaOH/SiO_2 = 0.25$$

$$H_2O/SiO_2 = 30;$$

after evenly mixing, the mixture was added in a stainless steel reactor and crystallized at 165° C. for 6 days. Upon completion of the crystallization, the product was filtered, washed, dried in an oven at 110° C. for 12 hours, and calcined in air at 550° C. for 5 hours to obtain a zeolite.

The XRD spectrum data of the dried sample are shown in Table I-12, and the SEM image of the sample is similar to that illustrated in FIG. 2.

TABLE I-12

XRD spectrum data of the resulting zeolite in Example I-12

| 2θ(°) | interplanar spacing (Å) | relative intensity ($I/I_0 \times 100$) |
|---|---|---|
| 9.20 | 9.608 | 53 |
| 12.78 | 6.919 | 46 |

TABLE I-12-continued

| XRD spectrum data of the resulting zeolite in Example I-12 | | |
|---|---|---|
| 2θ(°) | interplanar spacing (Å) | relative intensity ($I/I_0 \times 100$) |
| 16.86 | 5.254 | 28 |
| 19.25 | 4.606 | 67 |
| 23.68 | 3.754 | 38 |
| 24.18 | 3.678 | 35 |
| 26.04 | 3.419 | 100 |
| 30.79 | 2.902 | 6 |
| 36.97 | 2.429 | 5 |
| 43.58 | 2.077 | 6 |
| 48.72 | 1.868 | 9 |

The resulting calcined product has a specific surface area of 373 $m^2/g$, an external specific surface area of 148 $m^2/g$, a total pore volume of 0.75 $cm^3/g$, and a microporous volume of 0.09 $cm^3/g$. The sample has a nano-flake morphology and a crystal thickness of approximately 16 nanometers.

The calcined sample has a $SiO_2/Al_2O_3$=30.6 (molar ratio) and a $SiO_2/ZrO_2$=131.2 (molar ratio) measured using the inductively coupled plasma atomic emission spectroscopy (ICP).

The ammonia temperature programmed desorption ($NH_3$-TPD) spectrum of the resulting sample is similar to that illustrated in FIG. 4. A total acid content resulted therefrom is 773 $\mu mol \cdot g^{-1}$ with a weak acid content of 63%. The infrared spectrum of pyridine adsorption is similar to that illustrated in FIG. 5, and the Lewis/Bronsted acid ratio is analyzed and measured to be 2.8.

Example I-13

The test was carried out by reference to Example I-1, except that the used reactants and material ratios (molar ratio) were:

$$Al_2O_3/SiO_2 = 0.05$$

$$SnO_2/SiO_2 = 0.008$$

$$\text{Tetramethylammonium bromide } (A)/SiO_2 = 0.15$$

$$\text{n-octyltrimethylammonium bromide } (B)/SiO_2 = 0.20$$

$$NaOH/SiO_2 = 0.30$$

$$H_2O/SiO_2 = 25;$$

after evenly mixing, the mixture was added in a stainless steel reactor and crystallized at 160° C. for 7 days. Upon completion of the crystallization, the product was filtered, washed, dried in an oven at 110° C. for 12 hours, and calcined in air at 550° C. for 6 hours to obtain a zeolite.

The XRD spectrum data of the dried sample are shown in Table I-13, and the SEM image of the sample is similar to that illustrated in FIG. 2.

TABLE I-13

| XRD spectrum data of the resulting zeolite in Example I-13 | | |
|---|---|---|
| 2θ(°) | interplanar spacing (Å) | relative intensity ($I/I_0 \times 100$) |
| 9.26 | 9.516 | 57 |
| 12.85 | 6.890 | 55 |
| 16.86 | 5.254 | 26 |
| 19.22 | 4.616 | 69 |
| 23.65 | 3.758 | 35 |
| 24.18 | 3.678 | 34 |
| 25.98 | 3.426 | 100 |
| 30.58 | 2.921 | 8 |
| 36.88 | 2.414 | 7 |
| 48.70 | 1.867 | 11 |

The resulting calcined product has a specific surface area of 386 $m^2/g$, an external specific surface area of 154 $m^2/g$, a total pore volume of 0.73 $cm^3/g$, and a microporous volume of 0.10 $cm^3/g$. The sample has a nano-flake morphology and a crystal thickness of approximately 15 nanometers.

The calcined sample has a $SiO_2/Al_2O_3$=21.5 (molar ratio) and a $SiO_2/SnO_2$=126.4 (molar ratio) measured using the inductively coupled plasma atomic emission spectroscopy (ICP).

The ammonia temperature programmed desorption ($NH_3$-TPD) spectrum of the resulting sample is similar to that illustrated in FIG. 4. A total acid content resulted therefrom is 794 $\mu mol \cdot g^{-1}$ with a weak acid content of 66%. The infrared spectrum of pyridine adsorption is similar to that illustrated in FIG. 5, and the Lewis/Bronsted acid ratio is analyzed and measured to be 2.4.

Example I-14

The test was carried out by reference to Example I-8, except that the used reactants and material ratios (molar ratio) were:

$$Al_2O_3/SiO_2 = 0.04$$

$$Fe_2O_3/SiO_2 = 0.005$$

$$\text{Tetramethylammonium chloride } (A)/SiO_2 = 0.15$$

$$\text{Hexadecylpyridine hydroxide } (B)/SiO_2 = 0.25$$

$$NaOH/SiO_2 = 0.20$$

$$H_2O/SiO_2 = 30;$$

after evenly mixing, the mixture was added in a stainless steel reactor and crystallized at 165° C. for 7 days. Upon completion of the crystallization, the product was filtered, washed, dried in an oven at 110° C. for 12 hours, and calcined in air at 550° C. for 6 hours to obtain a zeolite.

The XRD spectrum data of the dried sample are shown in Table I-14, and the SEM image of the sample is similar to that illustrated in FIG. 2.

TABLE I-14

| XRD spectrum data of the resulting zeolite in Example I-14 | | |
|---|---|---|
| 2θ(°) | interplanar spacing (Å) | relative intensity ($I/I_0 \times 100$) |
| 9.24 | 9.536 | 52 |
| 12.95 | 6.837 | 47 |
| 16.78 | 5.279 | 31 |
| 19.22 | 4.616 | 65 |
| 23.61 | 3.765 | 35 |
| 24.10 | 3.691 | 35 |
| 25.88 | 3.439 | 100 |
| 30.46 | 2.932 | 8 |
| 36.84 | 2.416 | 8 |
| 43.21 | 2.100 | 7 |
| 48.47 | 1.876 | 11 |

The resulting calcined product has a specific surface area of 383 $m^2/g$, an external specific surface area of 155 $m^2/g$, a total pore volume of 0.75 $cm^3/g$, and a microporous volume of 0.10 $cm^3/g$. The sample has a nano-flake morphology and a crystal thickness of approximately 17 nanometers.

The calcined sample has a $SiO_2/Al_2O_3$=26.5 (molar ratio) and a $SiO_2/Fe_2O_3$=188.4 (molar ratio) measured using the inductively coupled plasma atomic emission spectroscopy (ICP).

The ammonia temperature programmed desorption ($NH_3$-TPD) spectrum of the resulting sample is similar to similar to that illustrated in FIG. 4. A total acid content resulted therefrom is 787 $\mu mol \cdot g^{-1}$ with a weak acid content of 68%. The infrared spectrum of pyridine adsorption is similar to that illustrated in FIG. 5, and the Lewis/Bronsted acid ratio is analyzed and measured to be 1.8.

Example I-15

The test was carried out by reference to Example I-1, except that the used reactants and material ratios (molar ratio) were:

$$Al_2O_3/SiO_2 = 0.045$$

$$\text{Tetramethylammonium hydroxide } (A)/SiO_2 = 0.45$$

$$\text{Dodecylpyridine bromide } (B)/SiO_2 = 0.20$$

$$NaOH/SiO_2 = 0.25$$

$$H_2O/SiO_2 = 25;$$

after evenly mixing, the mixture was added in a stainless steel reactor and crystallized at 160° C. for 6 days. Upon completion of the crystallization, the product was filtered, washed, dried in an oven at 110° C. for 12 hours, and calcined in air at 550° C. for 6 hours to obtain a zeolite.

The XRD spectrum data of the dried sample are shown in Table I-15, and the SEM image of the sample is similar to that illustrated in FIG. 2.

TABLE I-15

| XRD spectrum data of the resulting zeolite in Example I-15 | | |
|---|---|---|
| 2θ(°) | interplanar spacing (Å) | relative intensity ($I/I_0 \times 100$) |
| 9.29 | 9.485 | 51 |
| 12.82 | 6.906 | 49 |
| 14.08 | 6.282 | 9 |
| 16.81 | 5.270 | 32 |
| 19.25 | 4.607 | 66 |
| 23.66 | 3.757 | 36 |
| 24.05 | 3.698 | 37 |
| 25.89 | 3.438 | 100 |
| 30.44 | 2.936 | 8 |
| 43.48 | 2.086 | 6 |
| 48.55 | 1.873 | 10 |

The resulting calcined product has a specific surface area of 368 $m^2/g$, an external specific surface area of 145 $m^2/g$, a total pore volume of 0.72 $cm^3/g$, and a microporous volume of 0.09 $cm^3/g$. The sample has a nano-flake morphology and a crystal thickness of approximately 17 nanometers.

The calcined sample has a $SiO_2/Al_2O_3$=22.8 (molar ratio) measured using the inductively coupled plasma atomic emission spectroscopy (ICP).

The ammonia temperature programmed desorption ($NH_3$-TPD) spectrum of the resulting sample is similar to that illustrated in FIG. 4. A total acid content resulted therefrom is 861 $\mu mol \cdot g^{-1}$ with a weak acid content of 57%. The infrared spectrum of pyridine adsorption is similar to that illustrated in FIG. 5, and the Lewis/Bronsted acid ratio is analyzed and measured to be 2.0.

Example I-16

The test was carried out by reference to Example I-7. The used reactants and material ratios (molar ratio) were:

$$Al_2O_3/SiO_2 = 0.040$$

$$\text{Tetramethylammonium chloride } (A)/SiO_2 = 0.15$$

$$\text{Dodecylpyridine bromide } (B)/SiO_2 = 0.45$$

$$NaOH/SiO_2 = 0.15$$

$$H_2O/SiO_2 = 30;$$

after evenly mixing, the mixture was added in a stainless steel reactor and crystallized at 160° C. for 8 days. Upon completion of the crystallization, the product was filtered, washed, dried in an oven at 110° C. for 12 hours, and calcined in air at 550° C. for 6 hours to obtain a zeolite.

The XRD spectrum data of the dried sample are shown in Table I-16, and the SEM image of the sample is similar to that illustrated in FIG. 2.

TABLE I-16

| XRD spectrum data of the resulting zeolite in Example I-16 | | |
|---|---|---|
| 2θ(°) | interplanar spacing (Å) | relative intensity ($I/I_0 \times 100$) |
| 9.20 | 9.578 | 50 |
| 12.82 | 6.906 | 52 |
| 16.77 | 5.282 | 31 |
| 19.32 | 4.592 | 65 |
| 23.80 | 3.735 | 38 |

TABLE I-16-continued

| XRD spectrum data of the resulting zeolite in Example I-16 | | |
|---|---|---|
| 2θ(°) | interplanar spacing (Å) | relative intensity ($I/I_0 \times 100$) |
| 24.23 | 3.671 | 36 |
| 26.09 | 3.412 | 100 |
| 36.81 | 2.418 | 8 |
| 43.46 | 2.087 | 8 |
| 48.72 | 1.868 | 12 |

The resulting calcined product has a specific surface area of 388 $m^2/g$, an external specific surface area of 159 $m^2/g$, a total pore volume of 0.71 $cm^3/g$, and a microporous volume of 0.10 $cm^3/g$. The sample has a nano-flake morphology and a crystal thickness of approximately 17 nanometers.

The calcined sample has a $SiO_2/Al_2O_3$=26.1 (molar ratio) measured using the inductively coupled plasma atomic emission spectroscopy (ICP).

The ammonia temperature programmed desorption ($NH_3$-TPD) spectrum of the resulting sample is similar to that illustrated in FIG. 4. A total acid content resulted therefrom is 872 μmol·$g^{-1}$ with a weak acid content of 75%. The infrared spectrum of pyridine adsorption is similar to that illustrated in FIG. 5, and the Lewis/Bronsted acid ratio is analyzed and measured to be 3.0.

Example I-17

The test was carried out by reference to Example I-1, except that the used reactants and material ratios (molar ratio) were:

$$Al_2O_3/SiO_2 = 0.05$$

$$\text{Tetramethylammonium hydroxide } (A)/SiO_2 = 0.20$$

$$\text{Hexadecylpyridine chloride } (B)/SiO_2 = 0.25$$

$$NaOH/SiO_2 = 0.15$$

$$H_2O/SiO_2 = 20;$$

after evenly mixing, the mixture was added in a stainless steel reactor and crystallized at 160° C. for 7 days. Upon completion of the crystallization, the product was filtered, washed, dried in an oven at 110° C. for 12 hours, and calcined in air at 550° C. for 6 hours to obtain a zeolite.

The XRD spectrum data of the dried sample are shown in Table I-17, and the SEM image of the sample is similar to that illustrated in FIG. 2.

TABLE I-17

| XRD spectrum data of the resulting zeolite in Example I-17 | | |
|---|---|---|
| 2θ(°) | interplanar spacing (Å) | relative intensity ($I/I_0 \times 100$) |
| 9.22 | 9.557 | 50 |
| 12.88 | 6.874 | 52 |
| 14.05 | 6.296 | 10 |
| 16.74 | 5.292 | 31 |
| 19.35 | 4.585 | 65 |
| 23.82 | 3.732 | 38 |
| 24.25 | 3.668 | 36 |
| 26.11 | 3.409 | 100 |
| 30.47 | 2.932 | 8 |
| 36.84 | 2.416 | 8 |
| 48.49 | 1.875 | 12 |

The resulting calcined product has a specific surface area of 392 $m^2/g$, an external specific surface area of 159 $m^2/g$, a total pore volume of 0.72 $cm^3/g$, and a microporous volume of 0.09 $cm^3/g$. The sample has a nano-flake morphology and a crystal thickness of approximately 15 nanometers.

The calcined sample has a $SiO_2/Al_2O_3$=21.6 (molar ratio) measured using the inductively coupled plasma atomic emission spectroscopy (ICP).

The ammonia temperature programmed desorption ($NH_3$-TPD) spectrum of the resulting sample is similar to that illustrated in FIG. 4. A total acid content resulted therefrom is 908 μmol·$g^{-1}$ with a weak acid content of 79%. The infrared spectrum of pyridine adsorption is similar to that illustrated in FIG. 5, and the Lewis/Bronsted acid ratio is analyzed and measured to be 3.2.

Comparative Example I-1

The test was carried out by reference to Example I-1, except that the used reactants and material ratios (molar ratio) were:

$$Al_2O_3/SiO_2 = 0.22$$

$$\text{Tetramethylammonium hydroxide } (A)/SiO_2 = 0.15$$

$$\text{n-octyltrimethylammonium chloride } (B)/SiO_2 = 0.15$$

$$NaOH/SiO_2 = 0.30$$

$$H_2O/SiO_2 = 25;$$

after evenly mixing, the mixture was added in a stainless steel reactor and crystallized at 160° C. for 6 days. Upon completion of the crystallization, the product was filtered, washed, dried in an oven at 110° C. for 12 hours, and calcined in air at 550° C. for 6 hours to obtain a zeolite.

Figure 8:
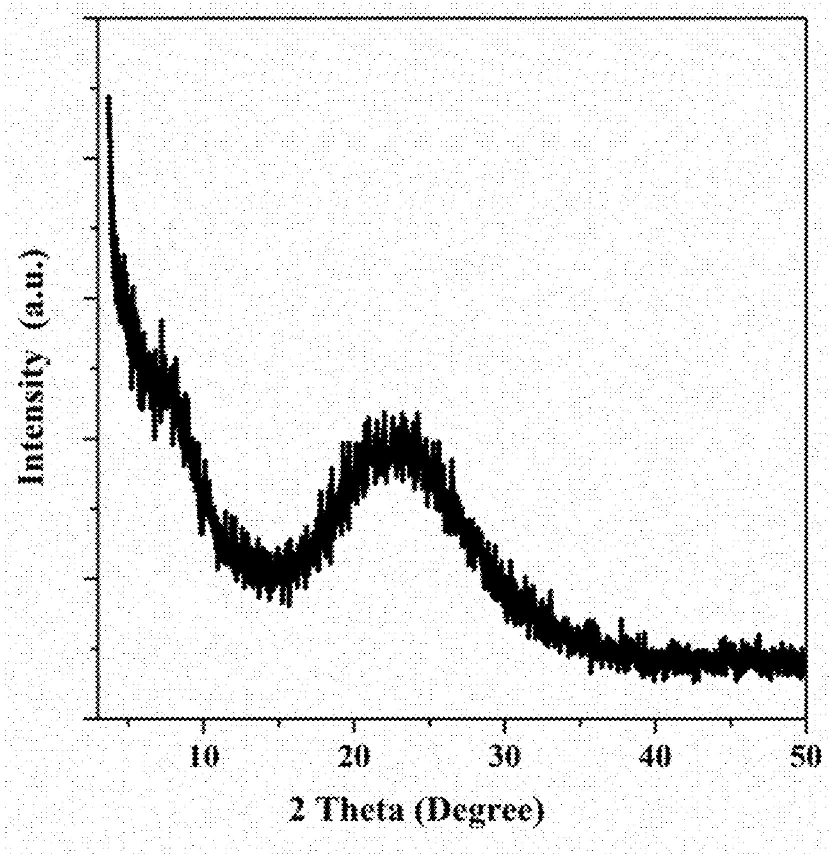
FIG. 8 illustrates the XRD spectrum of the sample obtained in Comparative Example I-1.

The XRD spectrum data of the dried sample are illustrated in FIG. 8. The dried sample is an amorphous material, not a SCM-36 zeolite.

Comparative Example I-2

The test was carried out by reference to Example I-1, except that the used reactants and material ratios (molar ratio) were:

$$Al_2O_3/SiO_2 = 0.05$$

$$\text{Tetramethylammonium hydroxide } (A)/SiO_2 = 0.15$$

$$\text{n-octyltrimethylammonium chloride } (B)/SiO_2 = 0.15$$

$$NaOH/SiO_2 = 0.55$$

$$H_2O/SiO_2 = 25;$$

after evenly mixing, the mixture was added in a stainless steel reactor and crystallized at 160° C. for 6 days. Upon completion of the crystallization, the product was filtered, washed, dried in an oven at 110° C. for 12 hours, and calcined in air at 550° C. for 6 hours to obtain a zeolite.

The XRD spectrum data of the dried sample are similar to that illustrated in FIG. 8. The dried sample is an amorphous material, not a SCM-36 zeolite.

Comparative Example I-3

The test was carried out by reference to Example I-1, except that octylamine was used as the organic structure directing agent (B) and the used reactants and material ratios (molar ratio) were:

$$Al_2O_3/SiO_2 = 0.05$$

$$\text{Tetramethylammonium hydroxide } (A)/SiO_2 = 0.15$$

$$\text{Octylamine } (B)/SiO_2 = 0.15$$

$$NaOH/SiO_2 = 0.30$$

$$H_2O/SiO_2 = 25;$$

after evenly mixing, the mixture was added in a stainless steel reactor and crystallized at 160° C. for 6 days. Upon completion of the crystallization, the product was filtered, washed, dried in an oven at 110° C. for 12 hours, and calcined in air at 550° C. for 6 hours to obtain a zeolite.

Figure 9:
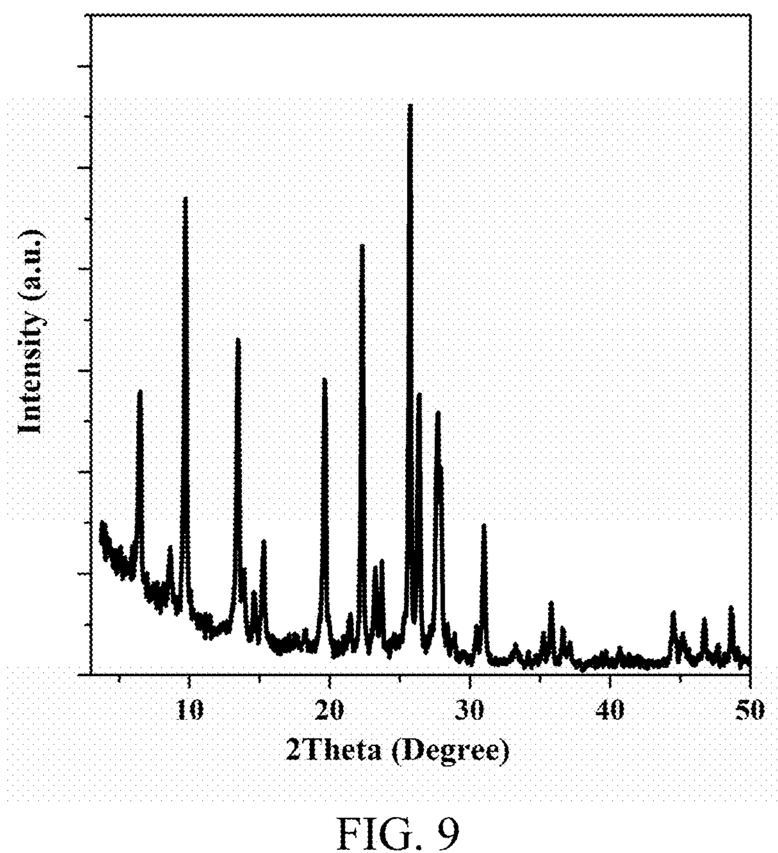
FIG. 9 illustrates the XRD spectrum of the sample obtained in Comparative Example I-3.

The XRD spectrum data of the dried sample are illustrated in FIG. 9. The dried sample is a mixture of MOR and a zeolite having another structure, not a SCM-36 zeolite.

Comparative Example I-4

The test was carried out by reference to Example I-1, except that only tetramethylammonium hydroxide was used as the organic structure directing agent and the used reactants and material ratios (molar ratio) were:

$$Al_2O_3/SiO_2 = 0.05$$

$$\text{Tetramethylammonium hydroxide}/SiO_2 = 0.15$$

$$NaOH/SiO_2 = 0.30$$

$$H_2O/SiO_2 = 25;$$

after evenly mixing, the mixture was added in a stainless steel reactor and crystallized at 160° C. for 6 days. Upon completion of the crystallization, the product was filtered, washed, dried in an oven at 110° C. for 12 hours, and calcined in air at 550° C. for 6 hours to obtain a zeolite.

Figure 10:
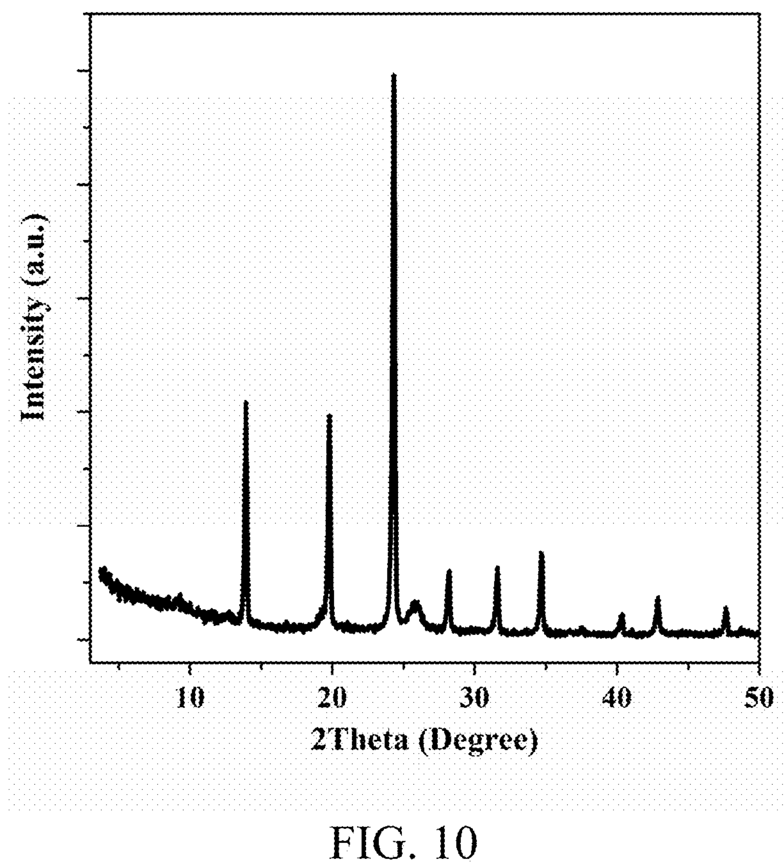
FIG. 10 illustrates the XRD spectrum of the sample obtained in Comparative Example I-4.

The XRD spectrum data of the dried sample are illustrated in FIG. 10. The dried sample is a mixture of SOD and a zeolite having another structure, not a SCM-36 zeolite.

Example I-18

The zeolite synthesized in Example I-5 was subjected to an ion exchange with a 0.5 mol/L $NH_4Cl$ solution (the mass ratio of the zeolite to the ammonium chloride solution being 1:20) at 70° C. for 2 hours, followed by centrifugating and washing. The sample resulted from two rounds of ion exchange was dried at 100° C. for 12 hours, and calcined at 550° C. for 6 hours to obtain a H-type SCM-36 zeolite.

The above calcined H-type SCM-36 zeolite powder sample was crushed, and a portion of the sample having a grain size of 20-40 mesh were sieved and placed in a fixed bed reactor for a pyrolysis reaction of isopropyl benzene. The reaction conditions were: a reaction temperature of 320° C., a reaction pressure of atmospheric pressure, and an isopropyl benzene weight hourly space velocity of 2 $h^{-1}$. The product was analyzed using Shimadzu GC-2014 gas chromatograph. After 1 hour of reaction, the conversion rate of isopropyl benzene was 25.2%, and the selectivity of benzene in the product was 94.1%.

In this example, the pyrolysis reaction of isopropyl benzene was carried out with isopropyl benzene as the raw material which was pyrolyzed into products such as propylene and benzene under the action of a catalyst.

$$\text{The conversion rate \% of isopropyl benzene} = (\text{molar amount of feed of isopropyl benzene} - \text{molar amount of isopropyl benzene in the product})/(\text{molar amount of feed of isopropyl benzene}) \times 100\%.$$

$$\text{The selectivity \% of benzene} = (\text{molar amount of benzene in the product})/(\text{total molar amount of aromatic hydrocarbons in the product}) \times 100\%;$$

wherein the aromatic hydrocarbons in the product do not include the raw material of isopropyl benzene.

Example I-19

The zeolite synthesized in Example I-5 was subjected to an ion exchange with a 0.5 mol/L $NH_4Cl$ solution (the mass ratio of the zeolite to the ammonium chloride solution being 1:20) at 70° C. for 2 hours, followed by centrifugating and washing. The sample obtained from two rounds of ion exchange was dried at 100° C. for 12 hours, and calcined at 550° C. for 6 hours to obtain a H-type SCM-36 zeolite.

The above calcined H-type SCM-36 zeolite powder sample was crushed, and a portion of the sample having a grain size of 20-40 mesh were sieved and placed in a fixed bed reactor for a methanol conversion reaction. The reaction conditions were: a reaction temperature of 460° C., a reaction pressure of 0.1 MPa, and a weight hourly space velocity of the raw material of methanol of 1 $h^{-1}$. The product was analyzed using Shimadzu GC-2014 gas chromatograph. After 45 min of reaction, the conversion rate of methanol was 99.0%, the selectivity of C2-C4 olefins in the product was 58.6%, and the selectivity of aromatic hydrocarbons was 4.2%.

In this example, the methanol conversion reaction was a conversion of the raw material of methanol to hydrocarbons such as olefins and aromatic hydrocarbons under the action of a catalyst.

$$\text{The conversion rate \% of methanol} = (\text{molar amount of feed of methanol} - \text{molar amount of methanol in the product} - 2 \times \text{molar amount of dimethyl ether in the product})/$$

-continued $$(\text{molar amount of feed of methanol}) \times 100\%;$$

$$\text{The selectivity \% of } C2-C4 \text{ olefins} = (2 \times \text{molar amount of } C2 \text{ olefin in the product} + 3 \times \text{molar amount of } C3 \text{ olefin in the product} + 4 \times \text{molar amount of } C4 \text{ olefin in the product}) / (\text{molar amount of feed of methanol} - \text{molar amount of methanol in the product} - 2 \times \text{molar amount of dimethyl ether in the product}) \times 100\%.$$

$$\text{The selectivity \% of aromatic hydrocarbons} = (6 \times \text{molar amount of benzene in the product} + 7 \times \text{molar amount of toluene in the product} + 8 \times \text{molar amount of xylene in the product}) / (\text{molar amount of feed of methanol} - \text{molar amount of methanol in the product} - 2 \times \text{molar amount of dimethyl ether in the product}) \times 100\%.$$

In the following examples and comparative examples, the reaction product of p-xylene was qualitatively analyzed by a gas chromatography-mass spectrometry (GC-MS), and the conversion rate of the substrate of 2,5-methylfuran and/or 2,5-hexanedione and the yield of the reaction product of pX were analyzed by a gas chromatography (GC). The gas chromatography-mass spectrometer was Agilent 7890A from Agilent in the United States; the chromatographic column was an HP-5 non-polar capillary column (30 m, 0.53 mm); the gas chromatographer was Agilent 7890B; the detector was a hydrogen flame ionization detector (FID); the chromatographic column was an SE-54 capillary column (30 m, 0.53 mm).

In the following examples and comparative examples, the formula for the conversion rate of 2,5-dimethylfuran (or 2,5-hexanedione) is:

$$\text{Conversion rate \% of 2,5-dimethylfuran (and/or 2,5-hexanedione)} = \text{molar amount of 2,5-dimethylfuran (and/or 2,5-hexanedione) participating in the reaction)} / (\text{molar amount of reaction substrate of 2,5-dimethylfuran (and/or 2,5-hexanedione)}) \times 100\%.$$

In the present application, the formula for calculating the yield of the product of p-xylene (pX) is:

$$\text{Yield \% of product of } pX = (\text{molar amount of } pX \text{ generated by the reaction}) / (\text{molar amount of reaction substrate of 2,5-dimethylfuran (and/or 2,5-hexanedione)}) \times 100\%.$$

In the present application, the formula for calculating the selectivity of the product of p-xylene is:

$$\text{Selectivity \% of product of } pX = (\text{molar amount of } pX \text{ generated by the reaction}) / (\text{molar amount of reacted 2,5-dimethylfuran (and/or 2,5-hexanedione)}) \times 100\%.$$

Example II-1 n-heptane was used as a reaction solvent, where the mass ratio of n-heptane to 2,5-dimethylfuran (DMF) was 20, and the mass ratio of DMF to the catalyst was 1. The reaction temperature was 240° C., and the reaction time was 24 hours. 1.0 g of the SCM-36 zeolite prepared in Example I-1, 1.0 g of DMF and 20 g of n-heptane were added to an autoclave with stirring, and 2.0 MPa ethylene was filled in. A temperature-programmed heating jacket was used to raise the temperature to a preset temperature, and then magnetic stirring was used for stirring. The reaction lasted for 24 hours under the condition of 240° C. The conversion rate of DMF was 86%, the pX selectivity was 94%, and the selectivity of the key impurity of polyalkylbenzene was less than 1% calculated based on the gas-phase analysis of the reaction liquid.

Example II-2 n-heptane was used as a reaction solvent, where the mass ratio of n-heptane to DMF was 20, and the mass ratio of DMF to the catalyst was 1. The reaction temperature was 240° C., and the reaction time was 24 hours. 1.0 g of the SCM-36 zeolite prepared in Example I-2, 1.0 g of DMF and 20 g of n-heptane were added to an autoclave with stirring, and 2.0 MPa ethylene was filled in. A temperature-programmed heating jacket was used to raise the temperature to a preset temperature, and then magnetic stirring was used for stirring. The reaction lasted for 24 hours under the condition of 240° C. The conversion rate of DMF was 90%, the pX selectivity was 94%, and the selectivity of the key impurity of polyalkylbenzene was less than 1% calculated based on the gas-phase analysis of the reaction liquid.

Example II-3 n-heptane was used as a reaction solvent, where the mass ratio of n-heptane to DMF was 20, and the mass ratio of DMF to the catalyst was 1. The reaction temperature was 240° C., and the reaction time was 24 hours. 1.0 g of the SCM-36 zeolite prepared in Example I-3, 1.0 g of DMF and 20 g of n-heptane were added to an autoclave with stirring, and 2.0 MPa ethylene was filled in. A temperature-programmed heating jacket was used to raise the temperature to a preset temperature, and then magnetic stirring was used for stirring. The reaction lasted for 24 hours under the condition of 240° C. The conversion rate of DMF was 86%, the pX selectivity was 95%, and the selectivity of the key impurity of polyalkylbenzene was less than 1% calculated based on the gas-phase analysis of the reaction liquid.

Example II-4 n-heptane was used as a reaction solvent, where the mass ratio of n-heptane to DMF was 20, and the mass ratio of DMF to the catalyst was 1. The reaction temperature was 240° C., and the reaction time was 24 hours. 1.0 g of the SCM-36 zeolite prepared in Example I-4, 1.0 g of DMF and 20 g of n-heptane were added to an autoclave with stirring, and 2.0 MPa ethylene was filled in. A temperature-programmed heating jacket was used to raise the temperature to a preset temperature, and then magnetic stirring was used for stirring. The reaction lasted for 24 hours under the condition of 240° C. The conversion rate of DMF was 92%, the pX selectivity was 95%, and the selectivity of the key impurity of polyalkylbenzene was less than 1% calculated based on the gas-phase analysis of the reaction liquid.

Example II-5 n-heptane was used as a reaction solvent in this example, where the mass ratio of n-heptane to DMF was 20, and the mass ratio of DMF to the catalyst was 1.5. The reaction temperature was 250° C., and the reaction time was 30 hours. 1.0 g of the SCM-36 zeolite catalyst prepared in Example I-1, 1.5 g of DMF and 30 g of n-heptane were added to an autoclave with stirring, and 3.0 MPa ethylene was filled in. A temperature-programmed heating jacket was used to raise the temperature to a preset temperature, and then magnetic stirring was used for stirring. The reaction lasted for 30 hours under the condition of 250° C. The conversion rate of DMF was 88%, the pX selectivity was 96%, and the selectivity of the key impurity of polyalkylbenzene was less than 1% calculated based on the gas-phase analysis of the reaction liquid.

Example II-6 n-heptane was used as a reaction solvent in this example, where the mass ratio of n-heptane to 2,5-hexanedione (HDO) was 20, and the mass ratio of HDO to the catalyst was 1. The reaction temperature was 230° C., and the reaction time was 20 hours. 1.0 g of the SCM-36 zeolite catalyst prepared in Example I-1, 1 g of HDO and 20 g of n-heptane were added to an autoclave with stirring, and 2.0 MPa ethylene was filled in. A temperature-programmed heating jacket was used to raise the temperature to a preset temperature, and then magnetic stirring was used for stirring. The reaction lasted for 20 hours under the condition of 230° C. The conversion rate of HDO was 86%, the pX selectivity was 95%, and the selectivity of the key impurity of polyalkylbenzene was less than 1% calculated based on the gas-phase analysis of the reaction liquid.

Example II-7 n-hexane was used as a reaction solvent in this example, where the mass ratio of n-hexane to DMF was 30, and the mass ratio of DMF to the catalyst was 2. The reaction temperature was 260° C., and the reaction time was 24 hours. 1.0 g of the SCM-36 zeolite catalyst prepared in Example I-1, 2.0 g of DMF and 60 g of n-hexane were added to an autoclave with stirring, and 4.0 MPa ethylene was filled in. A temperature-programmed heating jacket was used to raise the temperature to a preset temperature, and then magnetic stirring was used for stirring. The reaction lasted for 24 hours under the condition of 260° C. The conversion rate of DMF was 83%, the pX selectivity was 94%, and the selectivity of the key impurity of polyalkylbenzene was less than 1% calculated based on the gas-phase analysis of the reaction liquid.

Example II-8 n-hexane was used as a reaction solvent in this example, where the mass ratio of n-hexane to DMF was 20, and the mass ratio of DMF to the catalyst was 1.5. The reaction temperature was 240° C., and the reaction time was 30 hours. 1.0 g of the SCM-36 zeolite catalyst prepared in Example I-1, 1.5 g of DMF and 30 g of n-hexane were added to an autoclave with stirring, and 2.0 MPa ethylene was filled in. A temperature-programmed heating jacket was used to raise the temperature to a preset temperature, and then magnetic stirring was used for stirring. The reaction lasted for 30 hours under the condition of 240° C. The conversion rate of DMF was 88%, the pX selectivity was 93%, and the selectivity of the key impurity of polyalkylbenzene was less than 1% calculated based on the gas-phase analysis of the reaction liquid.

Example II-9

γ-valerolactone was used as a reaction solvent in this example, where the mass ratio of γ-valerolactone to HDO was 15, and the mass ratio of HDO to the catalyst was 2. The reaction temperature was 270° C., and the reaction time was 28 hours. 1.0 g of the SCM-36 zeolite catalyst prepared in Example I-1, 2 g of HDO and 30 g of γ-valerolactone were added to an autoclave with stirring, and 3.0 MPa ethylene was filled in. A temperature-programmed heating jacket was used to raise the temperature to a preset temperature, and then magnetic stirring was used for stirring. The reaction lasted for 28 hours under the condition of 270° C. The conversion rate of HDO was 89%, the pX selectivity was 95%, and the selectivity of the key impurity of polyalkylbenzene was less than 1% calculated based on the gas-phase analysis of the reaction liquid.

Example II-10

γ-valerolactone was used as a reaction solvent in this example, where the mass ratio of γ-valerolactone to DMF was 30, and the mass ratio of DMF to the catalyst was 3. The reaction temperature was 270° C., and the reaction time was 32 hours. 1.0 g of the SCM-36 zeolite catalyst prepared in Example I-1, 3.0 g of DMF and 90 g of γ-valerolactone were added to an autoclave with stirring, and 4.0 MPa ethylene was filled in. A temperature-programmed heating jacket was used to raise the temperature to a preset temperature, and then magnetic stirring was used for stirring. The reaction lasted for 32 hours under the condition of 270° C. The conversion rate of DMF was 85%, the pX selectivity was 94%, and the selectivity of the key impurity of polyalkylbenzene was less than 1% calculated based on the gas-phase analysis of the reaction liquid.

Example II-11

Toluene was used as a reaction solvent in this example, where the mass ratio of toluene to HDO was 22, and the mass ratio of HDO to the catalyst was 1. The reaction temperature was 250° C., and the reaction time was 18 hours. 1.0 g of the SCM-36 zeolite catalyst prepared in Example I-1, 1 g of HDO and 22 g of toluene were added to an autoclave with stirring, and 2.0 MPa ethylene was filled in. A temperature-programmed heating jacket was used to raise the temperature to a preset temperature, and then magnetic stirring was used for stirring. The reaction lasted for 18 hours under the condition of 250° C. The conversion rate of HDO was 93%, the pX selectivity was 95%, and the selectivity of the key impurity of polyalkylbenzene was less than 1% calculated based on the gas-phase analysis of the reaction liquid.

Example II-12

Toluene was used as a reaction solvent in this example, where the mass ratio of toluene to HDO was 25, and the mass ratio of HDO to the catalyst was 1.5. The reaction temperature was 260° C., and the reaction time was 24 hours. 1.0 g of the SCM-36 zeolite catalyst prepared in Example I-1, 1.5 g of HDO and 37.5 g of toluene were added to an autoclave with stirring, and 4.0 MPa ethylene was filled in. A temperature-programmed heating jacket was used to raise the temperature to a preset temperature, and then magnetic stirring was used for stirring. The reaction lasted for 24 hours under the condition of 260° C. The conversion rate of HDO was 90%, the pX selectivity was 95%, and the selectivity of the key impurity of polyalkylbenzene was less than 1% calculated based on the gas-phase analysis of the reaction liquid.

Example II-13

Cyclohexane was used as a reaction solvent in this example, where the mass ratio of cyclohexane to DMF was 30, and the mass ratio of DMF to the catalyst was 2. The reaction temperature was 250° C., and the reaction time was 40 hours. 1.0 g of the SCM-36 zeolite catalyst prepared in Example I-1, 2.0 g of DMF and 60 g of cyclohexane were added to an autoclave with stirring, and 4.0 MPa ethylene was filled in. A temperature-programmed heating jacket was used to raise the temperature to a preset temperature, and then magnetic stirring was used for stirring. The reaction lasted for 40 hours under the condition of 250° C. The conversion rate of DMF was 86%, the pX selectivity was 96%, and the selectivity of the key impurity of polyalkylbenzene was less than 1% calculated based on the gas-phase analysis of the reaction liquid.

Example II-14

Cyclohexane was used as a reaction solvent in this example, where the mass ratio of cyclohexane to HDO was 20, and the mass ratio of HDO to the catalyst was 2. The reaction temperature was 255° C., and the reaction time was 38 hours. 1.0 g of the SCM-36 zeolite catalyst prepared in Example I-1, 2.0 g of HDO and 40.0 g of cyclohexane were added to an autoclave with stirring, and 4.0 MPa ethylene was filled in. A temperature-programmed heating jacket was used to raise the temperature to a preset temperature, and then magnetic stirring was used for stirring. The reaction lasted for 38 hours under the condition of 255° C. The conversion rate of HDO was 87%, the pX selectivity was 95%, and the selectivity of the key impurity of polyalkylbenzene was less than 1% calculated based on the gas-phase analysis of the reaction liquid.

To provide a more intuitive description of the reaction conditions and the results of the above Examples II-1 to II-14, the various parameters and the results are listed in Table II-1.

TABLE II-1

Reaction conditions and results of Examples II-1 to II-14

| Example No. | reaction solvent | reaction substrate | source of catalyst | mass ratio of raw material to catalyst | mass ratio of organic solvent to raw material | reaction temperature (° C.) | reaction time (h) | ethylene pressure (MPa) | conversion rate (%) | pX selectivity (%)) |
|---|---|---|---|---|---|---|---|---|---|---|
| II-1 | n-heptane | DMF | Example I-1 | 1 | 20 | 240 | 24 | 2 | 86 | 94 |
| II-2 | n-heptane | DMF | Example I-2 | 1 | 20 | 240 | 24 | 2 | 90 | 94 |
| II-3 | n-heptane | DMF | Example I-3 | 1 | 20 | 240 | 24 | 2 | 86 | 95 |
| II-4 | n-heptane | DMF | Example I-4 | 1 | 20 | 240 | 24 | 2 | 92 | 95 |
| II-5 | n-heptane | DMF | Example I-1 | 1.5 | 20 | 250 | 30 | 3 | 88 | 96 |
| II-6 | n-heptane | HDO | Example I-1 | 1 | 20 | 230 | 20 | 2 | 86 | 95 |
| II-7 | n-hexane | DMF | Example I-1 | 2 | 30 | 260 | 24 | 4 | 83 | 94 |
| II-8 | n-hexane | DMF | Example I-1 | 1.5 | 20 | 240 | 30 | 2 | 88 | 93 |
| II-9 | γ-valerolactone | HDO | Example I-1 | 2 | 15 | 270 | 28 | 3 | 89 | 95 |
| II-10 | γ-valerolactone | DMF | Example I-1 | 3 | 30 | 270 | 32 | 4 | 85 | 94 |
| II-11 | toluene | HDO | Example I-1 | 1 | 22 | 250 | 18 | 2 | 93 | 95 |
| II-12 | toluene | HDO | Example I-1 | 1.5 | 25 | 260 | 24 | 4 | 90 | 95 |
| II-13 | cyclohexane | DMF | Example I-1 | 2 | 30 | 250 | 40 | 4 | 86 | 96 |
| II-14 | cyclohexane | HDO | Example I-1 | 2 | 20 | 255 | 38 | 4 | 87 | 95 |

Figure 11:
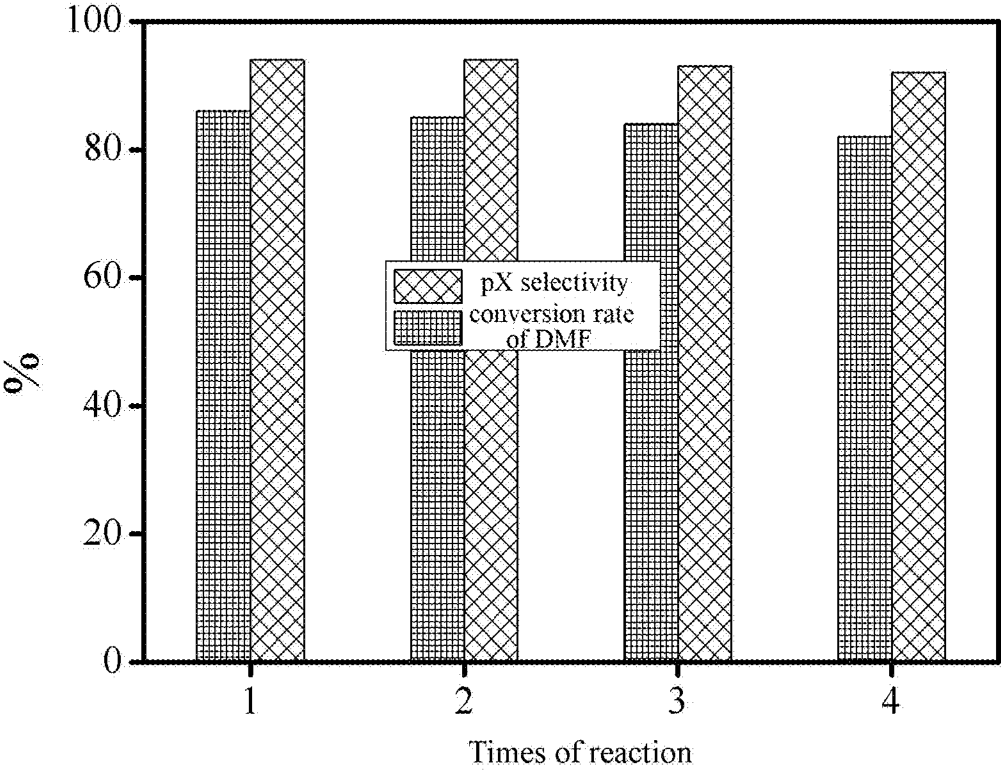
FIG. 11 is a graph of the conversion rate of 2,5-dimethylfuran and the p-xylene selectivity under the conditions of recycling the SCM-36 zeolite in Example II-15.

Example II-15 n-heptane was used as a reaction solvent, where the mass ratio of n-heptane to DMF was 20, and the mass ratio of DMF to the catalyst was 1. The reaction temperature was 240° C., and the reaction time was 24 hours. 1.0 g of the SCM-36 zeolite prepared in Example I-1, 1.0 g of DMF and 20.0 g of n-heptane were added to an autoclave with stirring, and 2.0 MPa ethylene was filled in. A temperature-programmed heating jacket was used to raise the temperature to a preset temperature, and then magnetic stirring was used for stirring. The reaction lasted for 24 hours under the condition of 240° C. The conversion rate of DMF and the pX selectivity were calculated based on the gas-phase analysis of the reaction liquid. The used catalyst was washed and then dried before proceeding to the next reaction, and the reaction was recycled for a total of 4 times. The results are as shown in FIG. 11. The results showed that after 4 times of reaction, the conversion rate of DMF remained 82% or more, the pX selectivity remained at 92%, and the selectivity of the key impurity of polyalkylbenzene was less than 1%, which indicated that the SCM-36 zeolite had a good cyclic stability.

Example II-16

1) Manufacture of a SCM-36 Zeolite

The test was carried out by reference to Example I-1, except that the used reactants and material ratios (molar ratio) were:

$$Al_2O_3/SiO_2 = 0.017$$

$$\text{Tetramethylammonium hydroxide } (A)/SiO_2 = 0.20$$

$$\text{n-octyltrimethylammonium chloride } (B)/SiO_2 = 0.25$$

$$NaOH/SiO_2 = 0.20$$

$$H_2O/SiO_2 = 30;$$

after evenly mixing, the mixture was added in a stainless steel reactor and crystallized at 155° C. for 8 days. Upon completion of the crystallization, the product was filtered, washed, dried in an oven at 120° C. for 6 hours, and calcined in air at 550° C. for 8 hours to obtain a zeolite.

The XRD spectrum data of the dried sample are shown in Table II-2, and the SEM image of the sample is similar to that illustrated in FIG. 2.

TABLE II-2

XRD spectrum data of the resulting zeolite in Example II-16

| 2θ(°) | interplanar spacing (Å) | relative intensity ($I/I_0 \times 100$) |
|---|---|---|
| 9.32 | 9.451 | 54 |
| 12.87 | 6.882 | 42 |
| 14.11 | 6.297 | 17 |
| 16.77 | 5.264 | 13 |
| 19.18 | 4.616 | 63 |
| 23.70 | 3.745 | 33 |
| 24.33 | 3.664 | 37 |
| 26.14 | 3.412 | 100 |
| 30.58 | 2.923 | 7 |
| 43.45 | 2.081 | 5 |
| 48.59 | 1.878 | 11 |

The resulting calcined product has a specific surface area of 372 ma/g, an external specific surface area of 149 ma/g, a total pore volume of 0.74 $cm^3/g$, and a microporous volume of 0.09 $cm^3/g$. The sample has a nano-flake morphology and a crystal thickness of approximately 12 nanometers. The calcined sample has a $SiO_2/Al_2O_3$=61.5 (molar ratio) measured using the inductively coupled plasma atomic emission spectroscopy (ICP).

Figure 12:
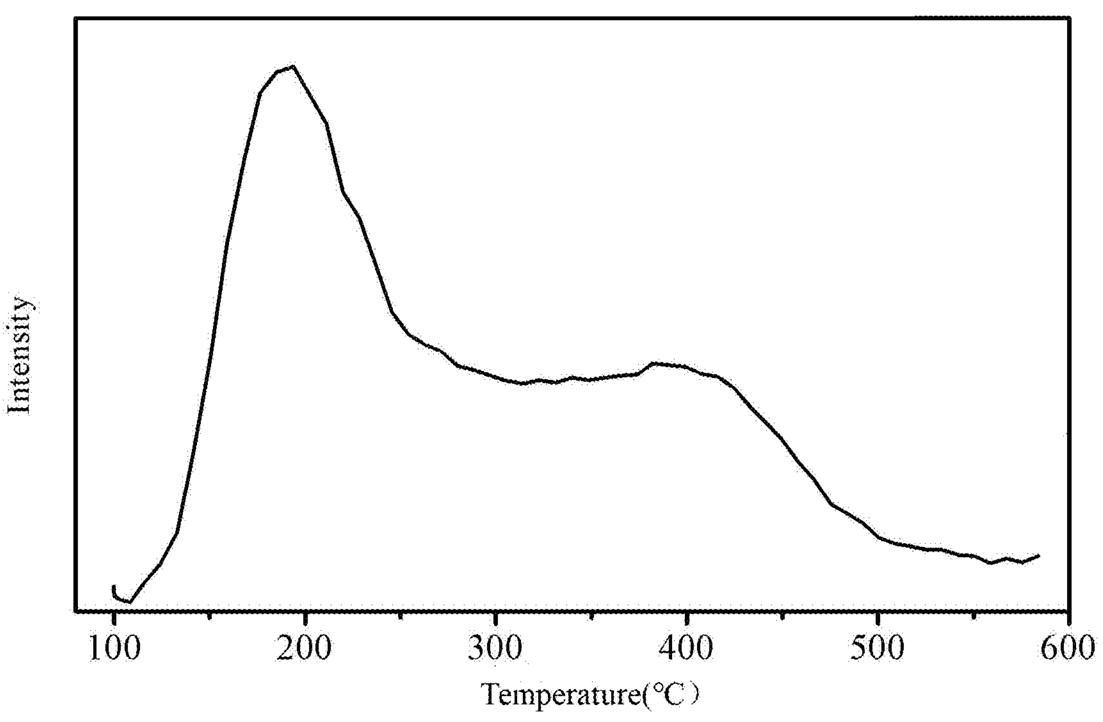
FIG. 12 illustrates the $NH_3$-TPD spectrum of the zeolite obtained in Example II-16.
Figure 13:
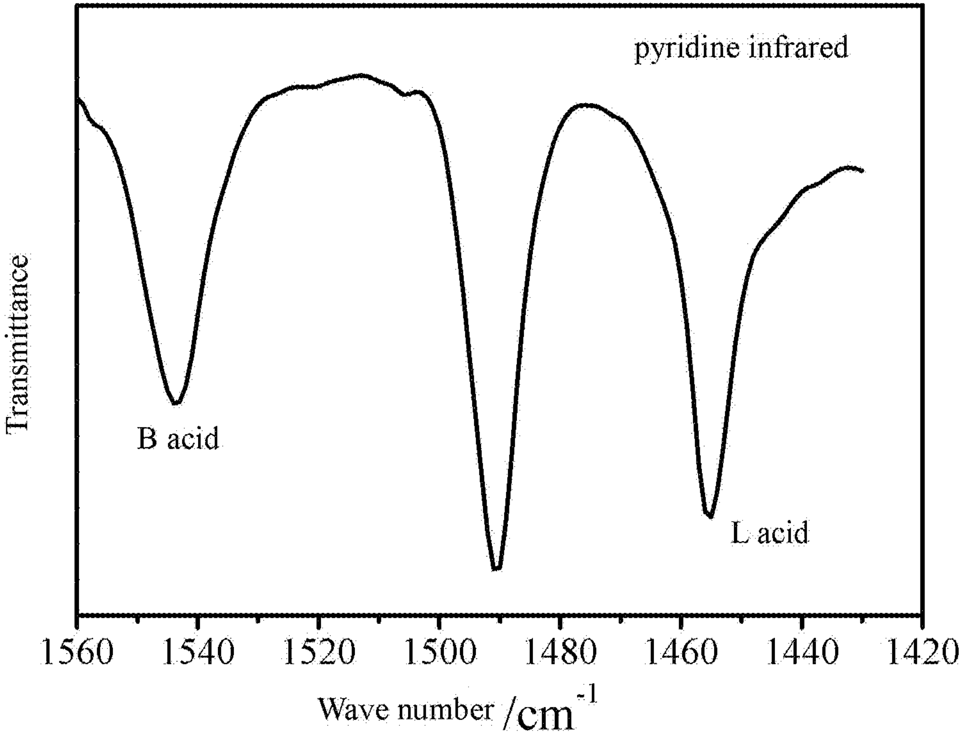
FIG. 13 illustrates the Py-FTIR spectrum of the zeolite obtained in Example II-16.

The ammonia temperature programmed desorption ($NH_3$-TPD) spectrum of the resulting sample is illustrated in FIG. 12. A total acid content resulted therefrom is 470·$\mu mol \cdot g^{-1}$ with a weak acid content of 47%. The infrared spectrum of pyridine adsorption is illustrated in FIG. 13, and the Lewis/Bronsted acid ratio is analyzed and measured to be 0.4.

2) Preparation of p-Xylene n-heptane was used as a reaction solvent. 1.0 g of the above manufactured SCM-36 zeolite, 1.0 g of DMF and 20 ml of n-heptane were added to an autoclave with stirring, and 2.0 MPa ethylene was filled in. A temperature-programmed heating jacket was used to raise the temperature to a preset temperature, and then magnetic stirring was used for stirring. The reaction lasted for 24 hours under the condition of 240° C. The conversion rate of DMF was 9300, the pX selectivity was 9000, and the selectivity of the key impurity of polyalkylbenzene was 3% calculated based on the gas-phase analysis of the reaction liquid.

Comparative Example II-1

The literature (Microporous and Mesoporous Materials, 2018, 263, 11-20) reported that AlPO-17 zeolite was produced. Phosphoric acid, aluminum isopropoxide, cyclohexylamine and deionized water were mixed evenly to form a gel according to $1P_2O_5$:$0.9Al_2O_3$:1 CHA (cyclohexylamine):$50H_2O$. Then AlPO-17 zeolite was produced by the hydrothermal crystallization at a temperature of 190° C. for 120 h, washing, drying, and calcining at 550° C. in air for 5 hours. The sample had a total acid content of 262 $\mu mol \cdot g^{-1}$ with a weak acid content of 93%, and a Lewis/Bronsted acid ratio of 4.2.

n-heptane was used as a reaction solvent. 1.0 g of the above produced catalyst, 1.0 g of DMF and 20 ml of n-heptane were added to an autoclave with stirring, and 2.0 MPa ethylene was filled in. A temperature-programmed heating jacket was used to raise the temperature to a preset temperature, and then magnetic stirring was used for stirring. The reaction lasted for 24 hours under the condition of 240° C. The conversion rate of DMF was 67% and the pX selectivity was 72% calculated based on the gas-phase analysis of the reaction liquid.

Preferred embodiments of the present application are described in detail as above. However, the present application is not limited to the specific details of the above embodiments. Within the scope of the technical concept of the present application, multiple simple modifications can be made to the technical solutions of the present application, all of which fall within the scope of protection of the present application.

Furthermore, it should be noted that the each of the specific technical features described in the above specific embodiments can be combined in any suitable manners in the absence of contradictions. In order to avoid unnecessary repetitions, the present application will not separately explain various possible combinations.

In addition, various different embodiments of the present application can also be combined arbitrarily. They should also be regarded as the content disclosed in the present application as long as they do not violate the ideas of the present application.

The invention claimed is:

1. A silicon-aluminum zeolite having a silicon/aluminum ratio n≥5, wherein an X-ray diffraction pattern of the silicon-aluminum zeolite has characteristic diffraction peaks with relative intensity as shown in the following table:

| 2θ(°) | relative intensity ($I/I_0 \times 100$) |
|---|---|
| 8.99-9.59 | S |
| 12.48-13.08 | s-vs |
| 18.91-19.51 | s-vs |
| 23.39-23.99 | M |
| 24.00-24.41 | M |
| 25.65-26.25 | Vs. |

2. The silicon-aluminum zeolite according to claim 1, wherein the X-ray diffraction pattern of the silicon-aluminum zeolite further comprises one or more characteristic diffraction peaks with relative intensity as shown in the following table:

| 2θ(°) | relative intensity ($I/I_0 \times 100$) |
|---|---|
| 16.50-17.10 | w-m |
| 48.33-48.93 | w-m. |

3. The silicon-aluminum zeolite according to claim 2, wherein the X-ray diffraction pattern of the silicon-aluminum zeolite further comprises characteristic diffraction peaks with relative intensity as shown in the following table:

| 2θ(°) | relative intensity ($I/I_0 \times 100$) |
|---|---|
| 13.65-14.25 | w |
| 30.23-30.83 | w |
| 36.67-37.27 | w |
| 43.05-43.65 | w. |

4. The silicon-aluminum zeolite according to claim 1, having at least one of following features:
- a specific surface area of 300-700 $m^2/g$;
- an external specific surface area 50-300 $m^2/g$;
- a total pore volume of 0.20-1.50 $cm^3/g$;
- a micropore volume of 0.05-0.35 $cm^3/g$;
- a total acid content of 400-1200 $\mu mol \cdot g^{-1}$, wherein a weak acid content is ≥40%; and
- a Lewis acid/Bronsted acid ratio of 0.1 to 3.8.

5. The silicon-aluminum zeolite according to claim 1, having a nano-flake crystal morphology with a crystal thickness of <30 nanometers.

6. The silicon-aluminum zeolite according to claim 1, further comprising at least one element M selected from the group consisting of titanium, boron, zirconium, tin, and iron.

7. A method for manufacturing the silicon-aluminum zeolite according to claim 1, comprising following steps:
1) crystallizing a mixture containing a silicon source, an aluminum source, an organic structure directing agent (A), an organic structure directing agent (B), an alkali source and water to obtain a zeolite; and
2) optionally, calcining the zeolite obtained in step 1) to obtain the silicon-aluminum zeolite, wherein, the organic structure directing agent (A) is selected from tetramethylammonium compounds, and the organic structure directing agent (B) is selected from C6-16 alkylpyridinium compounds, n-octyltrimethylammonium compounds, or a combination thereof.

8. The method according to claim 7, wherein in the mixture of step 1), a molar ratio of the silicon source (calculated based on $SiO_2$), the aluminum source (calculated based on $Al_2O_3$), the organic structure directing agent (A), the organic structure directing agent (B), the alkali source and water is 1:(0.01-0.20):(0.05-0.80):(0.05-0.80):(0.05-0.50):(8-80).

9. The method according to claim 7, wherein a crystallization temperature in step 1) is 120-200° C. and a crystallization time is 1-15 days.

10. The method according to claim 7, wherein the organic structure directing agent (A) is selected from a group consisting of tetramethylammonium hydroxide, tetramethylammonium chloride, tetramethylammonium bromide, tetramethylammonium iodide, or a combination thereof; and/or,
- the organic structure directing agent (B) is selected from a group consisting of hexadecylpyridine bromide, tetradecylpyridine bromide, dodecylpyridine bromide, decylpyridine bromide, hexadecylpyridine chloride, tetradecylpyridine chloride, hexadecylpyridine hydroxide, n-octyltrimethylammonium chloride, n-octyltrimethylammonium bromide, n-octyltrimethylammonium hydroxide, or a combination thereof.

11. The method according to claim 7, wherein the silicon source is selected from a group consisting of silicic acid, silica gel, silica sol, tetraethyl silicate, sodium silicate, and a combination thereof;
- the aluminum source is selected from a group consisting of aluminum hydroxide, aluminum oxide, aluminate, aluminum salt, tetraalkoxy aluminum, and a combination thereof; and/or
- the alkali source is selected from a group consisting of an inorganic alkali with an alkali metal as cation, an inorganic alkali with an alkali earth metal as cation, and a combination thereof.

12. The method according to claim 7, wherein the mixture according to step 1) further comprises a source of element M selected from a group consisting of titanium, boron, zirconium, tin, iron, and a combination thereof.

13. A zeolite composition comprising the silicon-aluminum zeolite according to claim 1 and a binder.

14. A method for removing one or more components from a mixture in a gas or a liquid phase, comprising contacting the mixture with an adsorbent, wherein the adsorbent comprises the silicon-aluminum zeolite according to claim 1.

15. A method for preparing p-xylene, comprising a step of reacting a raw material comprising 2,5-dimethylfuran, 2,5-hexanedione, or a combination thereof in contact with ethylene in the presence of a catalyst comprising or consisting of the silicon-aluminum zeolite according to claim 1.

16. The method according to claim 5, having at least one of following features:
- the reaction is carried out in the presence of an organic solvent selected from a group consisting of n-hexane, n-heptane, γ-valerolactone, tetrahydrofuran, toluene, cyclohexane, and a combination thereof;
- a mass ratio of the raw material to the catalyst is 0.6-30:1; and
- a mass ratio of the organic solvent to the raw material is 8-60:1.

17. The method according to claim 15, conditions of the reaction including:
- a reaction temperature is 160-340° C.;
- a reaction time is 6-64 hours; and
- a reaction pressure is 1-8 MPa.

18. The silicon-aluminum zeolite according to claim 1, wherein n is in the range of 5-80.

19. A catalyst carrier comprising the silicon-aluminum zeolite according to claim 1.

20. A catalyst comprising the catalyst carrier of claim 19 and an active ingredient supported on the catalyst carrier.

* * * * *